United States Patent [19]

Schuetz et al.

[11] Patent Number: 5,371,268
[45] Date of Patent: Dec. 6, 1994

[54] ORTHO-SUBSTITUTED BENZYL ESTERS OF CYCLOPROPANECARBOXYLIC ACIDS

[75] Inventors: Franz Schuetz, Ludwigshafen; Hubert Sauter, Mannheim; Norbert Goetz, Worms; Jochen Wild, Ruppertsberg; Hans-Josef Wolf, Maxdorf; Reinhard Doetzer, Weinheim; Gisela Lorenz, Neustadt; Eberhard Ammermann, Ludwigshafen; Christoph Kuenast, Otterstadt; Uwe Kardorff, Mannheim, all of Germany

[73] Assignee: BASF Aktiengesellschaft, Ludwigshafen, Germany

[21] Appl. No.: 209,358

[22] Filed: Mar. 14, 1994

Related U.S. Application Data

[63] Continuation of Ser. No. 37,538, Mar. 26, 1993, abandoned, which is a continuation of Ser. No. 708,770, May 28, 1991, abandoned.

[30] Foreign Application Priority Data

May 31, 1990 [DE] Germany .............. 4017488
Jul. 30, 1990 [DE] Germany .............. 4024094

[51] Int. Cl.⁵ .............................. C07C 69/76
[52] U.S. Cl. .......................... 560/35; 560/60; 556/35
[58] Field of Search ............. 560/35, 60; 556/35; 514/523, 531

[56] References Cited

U.S. PATENT DOCUMENTS

| 4,515,808 | 5/1985 | Elliott et al. | |
|---|---|---|---|
| 4,952,720 | 8/1990 | Schuetz et al. | 560/106 |
| 5,051,447 | 9/1991 | Wenderoth et al. | 560/35 |

FOREIGN PATENT DOCUMENTS

| 310954 | 10/1987 | European Pat. Off. | |
|---|---|---|---|
| 0354571 | 2/1990 | European Pat. Off. | |
| 0354571 | 10/1989 | Germany | 560/62 |

Primary Examiner—Marianne M. Cintins
Assistant Examiner—Keith MacMillan
Attorney, Agent, or Firm—Oblon, Spivak, McClelland, Maier & Neustadt

[57] ABSTRACT

Ortho-substituted benzyl esters of cyclopropanecarboxylic acids I

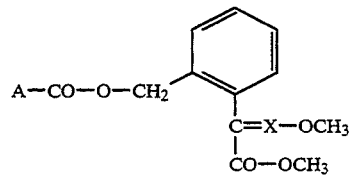

where X is N or CH and A is one of the following cyclopropane radicals:

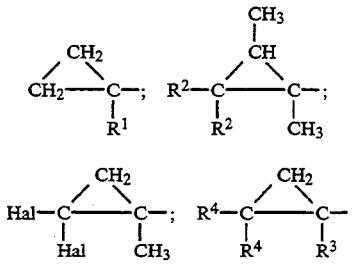

where $R^1$ is CN, $C_2$–$C_8$-alkyl, $CF_3$, $C_3$–$C_8$-alkenyl, ($C_1$–$C_4$-alkoxycarbonyl, unsubstituted or substituted phenyl-$C_1$–$C_6$-alkyl or phenyl-$C_3$–$C_6$-alkenyl, ethoxyphenyl, 2- or 3-bromophenyl, 2- or 4-trifluoromethylphenyl, 2,4- or 2,6-difluorophenyl, 2-floro-6-chlorophenyl, 2,4- or 2,6-dimethylphenyl, 2,3,6-trichlorophenyl or trimethylsilyl, $R^2$ is H or halogen, $R^3$ is unsubstituted or substituted phenyl, $R^4$ is $CH_3$ or halogen and Hal is halogen, with the proviso that X is CH when $R^1$ is $CF_3$ or trimethylsilyl, are suitable as fungicides and for controlling pests.

9 Claims, No Drawings

ORTHO-SUBSTITUTED BENZYL ESTERS OF CYCLOPROPANECARBOXYLIC ACIDS

This application is a continuation of application Ser. No. 08/037,538, filed on Mar. 26, 1993, now abandoned, which is a continuation of Ser. No. 07/708,770 filed May 28, 1991 now abandoned.

The present invention relates to novel orthosubstituted benzyl esters of cyclopropanecarboxylic acids of the general formula I

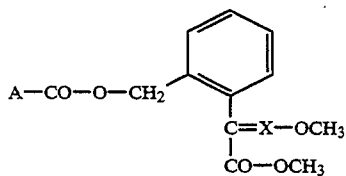

where X is nitrogen or =CH— and A is one of the following cyclopropane radicals:

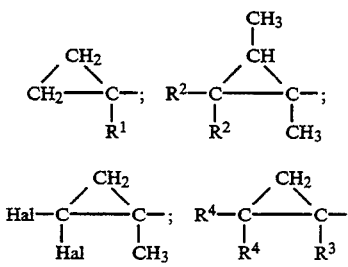

where $R^1$ is cyano, $C_2$–$C_8$-alkyl, trifluoromethyl, $C_3$–$C_8$-alkenyl, trimethylsilyl, $C_1$–$C_4$-alkoxycarbonyl, phenyl-$C_1$–$C_6$alkyl or phenyl-$C_3$–$C_6$-alkenyl, where each aromatic moiety may furthermore carry 1–5 halogen atoms or up to 3 of the following substituents: $C_1$–$C_6$-alkyl, partially or completely halogenated $C_1$–$C_6$-alkyl or $C_1$–$C_6$-alkoxy, ethoxyphenyl, 2-bromophenyl, 3-bromophenyl, 2-trifluoromethyiphenyl, 4-trifluoromethylphenyl, 2,4-difluorophenyl, 2,6,-difluorophenyl, 2-fluoro-6-chlorophenyl, 2,4-dimethylphenyl, 2,6-dimethylphenyl or 2,3,6-trichlorophenyl, $R^2$ is hydrogen or halogen, $R^3$ is phenyl which may carry 1–5 halogen atoms or up to 3 of the following substituents: $C_1$–$C_6$-alkyl, partially or completely halogenated $C_1$–$C_6$-alkyl or $C_1$–$C_6$-alkoxy, $R^4$ is methyl or halogen and Hal is halogen, with the proviso that X is =CH— when $R^1$ is trifluoromethyl or trimethylsilyl.

The present invention furthermore relates to a process for the preparation of these compounds, their use as fungicides and for controlling pests, and fungicities and pesticides which contain these compounds as active substances.

EP-A 310 954 and EP-A 354 571 disclose, intel alia, fungicidal ortho-substituted benzyl esters cyclopropanecarboxylic acids which are of the same as the compounds I and whose cyclopropane ring is stituted or methyl- or dichloro-substituted or carries a phenyl radical having various substituents. Furthermore, EP-A 354 571 discloses, inter alia, 2-[1-trifluoromethylcyclopropylcarbonyloxymethyl]-phenyl-and2-[1-trimethylsilylcyclopropylcarbonyloxymethyl]-phenylglyoxylic acid methyl ester O-methyloxime. The stated publications do not disclose any insecticidal activity.

It is an object of the present invention to provide novel ortho-substituted benzyl esters of cyclopropanecarboxylic acids.

We have found that this object is achieved by the ortho-substituted benzyl esters of cyclopropanecarboxylic acids of the formula I which are defined at the outset.

In the novel compounds I, the substituents have the following specific meanings:

$R^1$ is cyano;

branched or straight-chain $C_2$–$C_8$-alkyl, in particular $C_2$–$C_6$-alkyl, such as methyl, ethyl, isopropyl, n-butyl, tertbutyl, n-pentyl, isopentyl or neopentyl;

branched or straight-chain $C_3$–$C_6$-alkenyl, in particular $C_3$–$C_6$-alkenyl, such as prop-2-enyl, 1-methylprop-2-enyl, but-2-enyl, 3-methylbut-2-enyl or 2-methylprop-2-enyl; $C_1$–$C_4$-alkoxycarbonyl, in particular methoxycarbonyl or ethoxycarbonyl;

phenyl-$C_1$–$C_6$-alkyl or phenyl-$C_3$–$C_6$-alkenyl, in particular phenyl-$C_1$–$C_4$-alkyl or phenyl-$C_3$- or -$C_4$-alkenyl, such as benzyl, 2-phenylethyl, 3-phenyl-n-propyl, 4-phenyl-n-butyl, 3-phenylallyl or 4-phenylbut-2-enyl, where each aromatic moiety may furthermore carry 1–5 halogen atoms, such as fluorine, chlorine or bromine, or up to 3 of the following substituents:

branched or straight-chain $C_1$–$C_6$-alkyl, in particular $C_1$–$C_4$-alkyl, such as methyl, ethyl, n-propyl, isopropyl, n-butyl, sec-butyl or tert-butyl, partially or completely halogenated, branched or straight-chain $C_1$–$C_6$-alkyl, in particular $C_1$–$C_4$-alkyl, such as difluoromethyl, trifluoromethyl, trichloromethyl, pentafluoroethyl or 2-chloro-1,1,2-trifluoroethyl, or branched or straight-chain $C_1$–$C_6$-alkoxy, in particular $C_1$–$C_4$-alkoxy, such as methoxy, ethoxy, n-propoxy, isopropoxy, n-butoxy or tert-butoxy;

ethoxyphenyl, such as 2-, 3- or 4-ethoxyphenyl;

2- or 3-bromophenyl;

2- or 4-trifluoromethylphenyl;

2,4- or 2,6-difluorophenyl;

2-fluoro-6-chlorophenyl;

2,4- or 2,6-dimethylphenyl;

2,3,6-trichlorophenyl or trimethylsilyl or trifluoromethyl;

$R^2$ is hydrogen or halogen, such as fluorine, chlorine or bromine;

$R^3$ is phenyl which may carry 1–5 halogen atoms, such as fluorine, chlorine or bromine, or up to 3 of the following substituents:

branched or straight-chain $C_1$–$C_6$alkyl, in particular $C_1$–$C_4$-alkyl, such as methyl, ethyl, n-propyl, isopropyl, n-butyl, sec-butyl or tert-butyl, partially or completely halogenated, branched or straight-chain $C_1$–$C_6$alkyl, in particular $C_1$–$C_4$-alkyl, such as difluoromethyl, trifluoromethyl, chloromethyl, trichloromethyl, pentafluoroethyl or 2-chloro-1,1,2-trifluoroethyl, or branched or straight-chain $C_1$–$C_6$alkoxy, in particular $C_1$–$C_4$-alkoxy, such as methoxy, ethoxy, n-propoxy, isopropoxy, n-butoxy or tert-butoxy, preferred groups being 2-, 3- and 4-fluorophenyl, 2-, 3- and 4-chlorophenyl, 2-, 3- and 4-bromophenyl, 2-, 3- and 4-methylphenyl, 4-tert-butylphenyl, 2-, 3- and 4-trifluoromethylphenyl, 2-, 3- and 4-methoxyphenyl, 2-, 3- and 4-ethoxyphenyl, 2,4-difluorophenyl, 2,6-difluorophenyl, 2,4-dichlorophenyl, 3,4-dichlorophenyl, 2,6-dichlorophenyl, 2-fluoro-6-chlorophenyl, 2,3,6-trichlorophenyl, 2,4-, 3,4- and 2,6-dimethylphenyl, 2,4-, 3,4- and 2,6-dimethoxyphenyl and 3,4-diethoxyphenyl;

$R^4$ is methyl or halogen, such as fluorine, chlorine or bromine, and

Hal is halogen, such as fluorine, chlorine or bromine.

Particularly suitable compounds I are shown in Table 1. Compounds Ia whose cyclopropane ring is monosubstituted by the following radicals $R^{1'}$ are preferred:

cyano;

$C_2$–$C_4$-alkyl, such as ethyl, n-propyl, isopropyl or tert-butyl;

trifluoromethyl;

$C_3$- or $C_4$-alkenyl, such as prop-2-enyl or but-2-enyl;

methoxycarbonyl or ethoxycarbonyl;

phenyl-$C_1$–$C_4$-alkyl or phenyl-$C_3$- or -$C_4$-alkenyl, where each aromatic moiety may furthermore carry one of the following substituents:

halogen, such as fluorine, chlorine or bromine, or methyl, in particular benzyl, 3- or 4-fluorobenzyl, 3- or 4-chlorobenzyl, 4-bromobenzyl, 3-methylbenzyl, 3-(4-fluorophenyl)-propyl, 3-(4-chlorophenyl)-propyl, 3-(4-fluorophenyl)-prop-2-enyl or 3-(4-chlorophenyl)-prop-2enyl;

2-bromophenyl;

2,4- or 2,6-difluorophenyl;

2-fluoro-6-chlorophenyl;

2,3,6-trichlorophenyl and trimethylsilyl.

If $R^{1'}$ is phenylalkenyl, the E configuration at the double bond is particularly preferred.

The novel compounds I may be obtained as E/Z isomer mixtures in the preparation, owing to the substituent —C(COOCH$_3$)=X—OCH$_3$ ortho to the benzyl moiety. The isomers can, if desired, be separated by the conventional methods, for example by crystallization or chromatography. Compounds having the E configuration are particularly preferred.

In compounds I whose cyclopropane ring carries various substituents in the 2- and 3-positions, two configurations are also possible in the 1-position of the cyclopropane ring (which position carries the benzyl ester group). If the cyclopropane ring carries a methyl group in the 2-position (compounds Ib of Table 2), particularly preferred compounds are those in which the methyl group is in the trans position with respect to the benzyl ester group of the parent structure.

The ortho-substituted benzyl esters of cyclopropanecarboxylic acids I are obtainable in various ways, preferably by converting a cyclopropanecarboxylic acid II with a base in a conventional manner, in an inert solvent, such as ethanol, into the carboxylate anion and reacting this anion with an ortho-substituted benzyl compound III (cf. Synthesis 1975, 805):

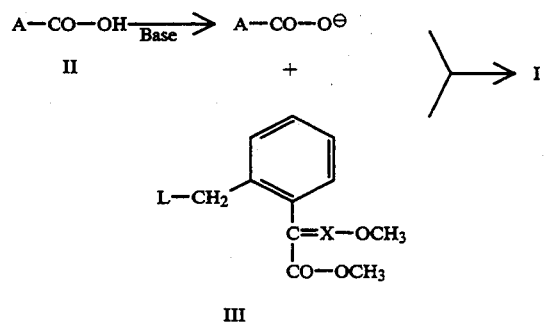

L is a nucleophilic leaving group, in particular sulfonyl, such as methanesulfonyl, trifluoromethylsulfonyl, p-toluenesulfonyl or p-bromophenylsulfonyl, or a methylsulfate radical, particularly preferably halogen, such as chlorine, bromine or iodine.

Particularly suitable bases are alkali metal hydroxides, such as sodium hydroxide and potassium hydroxide, and triethylamine.

The reaction of the carboxylate anion with the benzyl compound III is advantageously carried out in a solvent or diluent, such as acetone, acetonitrile, dimethyl sulfoxide, dioxane, dimethylformamide, N-methylpyrrolidone, N,N'-dimethylpropyleneurea or pyridine or, using a phase transfer catalyst, in a 2-phase system consisting of water and a hydrocarbon, such as carbon tetrachloride.

Examples of suitable phase transfer catalysts are trioctylpropylammonium chloride and cetyltrimethylammonium chloride (cf. Synthesis 1974, 867).

Advantageously, all starting compounds are used in a roughly stoichiometric ratio, but an excess of one or other component, for example of up to 10%, may also be advisable in some cases.

In general, the reaction temperature is from 0° C. to the boiling point of the solvent, preferably from 20° to 130° C.

Since the reaction is not pressure-dependent, it is advantageously carried out at atmospheric pressure.

The cyclopropanecarboxylic acids II are known or can be prepared by known processes [cf. for example Synthesis (1987), 738; Zh. Org. Khim 16 (1980), 2086; J. Am. Chem. Soc. 106 (1984), 6642; Chem. Ber. 116 (1983), 3895; Helv. Chim. Acta 69 (1986), 1655; Chem. Bet. (1986), 3694; Chem. Letters (1989), 475; J. Organometal. Chq. 46 (1972), 73; Gazz. Chim. Ital. 100 (1970), 566; J. Org. Chem. 48 (1983), 2472 and J. Org. Chem. 47 ( 1982 ), 893].

The ortho-substituted benzyl compounds III (where X is CH and L is chlorine or bromine) are likewise known or can be prepared by known processes (cf. for example DE-A 35 19 280, DE-A 35 45 318 and DE-A 35 45 319).

For example, the ortho-substituted benzyl bromide III (where X is CH and L is bromine) can be obtained by brominating the corresponding ortho-substituted toluene IV with N-bromosuccinimide (cf. Angew. Chem. 71 (1959), 349):

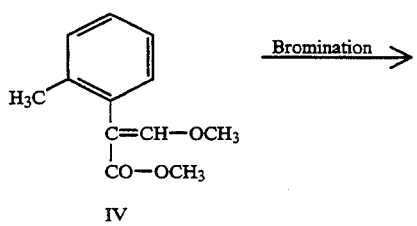

IV

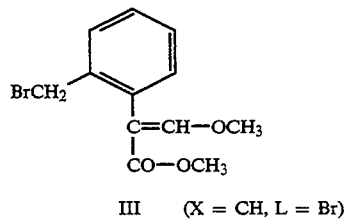

III    (X = CH, L = Br)

The ortho-substituted toluene IV can be prepared by a method in which, for example, a hydroxymethylene derivative Va, which is in equilibrium with the corresponding formyl derivative Vb, is alkylated in the presence of a base, such as potassium carbonate:

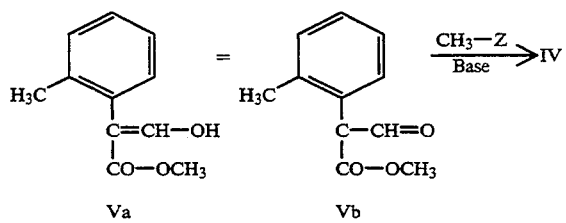

Z is methylsulfate, chloride, bromide or iodide.

Examples of suitable alkylating agents are dimethyl sulfate and methyl iodide, chloride and bromide.

The reaction is usually carried out in an inert solvent, for example in acetone.

The reaction temperature is in general from 20° to 60° C.

The hydroxymethylene derivative Va is obtainable, for example, by base-catalyzed reaction of methyl 2-methylphenylacetate with methyl formate in an inert solvent, such as diethyl ether or tetrahydrofuran, and sodium hydroxide, for example, can be used as the base (cf. Ann. Chem. 424 (1921), 214).

Ortho-substituted benzyl compounds III, where X is nitrogen and L is chlorine or bromine, are obtainable by various methods, advantageously by halogenating 2-methylphenylglyoxylic acid methyl esters O-methyloxime VI.

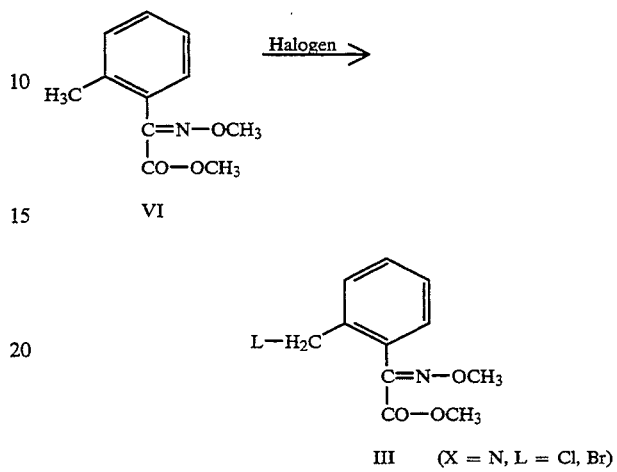

Chlorine or bromine in an inert solvent, e.g. tetrachloromethane, or halogenating agents, such as N-chloro- and N-bromosuccinimide [cf. Angew. Chem. 71 (1959), 349], in CCl₄ can be used for the halogenation. When elemental chlorine or bromine is used, it is advisable to carry out the reaction photochemically by exposure to sunlight.

The 2-methylphenylglyoxylic acid methyl ester O-methyloxime VI disclosed in DE-A 36 23 921 is advantageously obtainable from methyl 2-methylphenylglyoxylate by reaction with O-methylhydroxylamine hydrochloride or hydroxylamine hydrochloride, the primary product in this case being an oxime, which is then treated with a methylating agent, such as methyl chloride, methyl bromide, methyl iodide or dimethyl sulfate.

In a possible process variant for the preparation of the benzyl compounds III (where Y is nitrogen and L is chlorine or bromine), the methyl 2-methylphenylglyoxylate VII disclosed in DE-A 36 23 921 is first halogenated by one of the methods described above and the product is converted into the corresponding oxime:

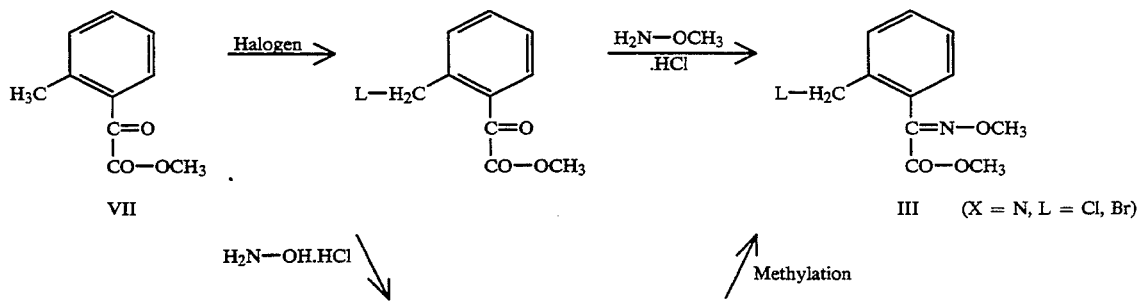

-continued

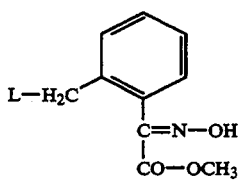

The ortho-substituted benzyl compounds III where the leaving group L is a p-toluenesulfonate, p-bromophenylsulfonate, methanesulfonate or trifluoromethanesulfonate radical can be prepared from the benzyl compounds III where L is chlorine or bromine by reaction with p-toluenesulfonic acid, p-bromophenylsulfonic acid, methanesulfonic acid or trifluoromethanesulfonic acid.

The reaction is advantageously carried out in a solvent or diluent, e.g. dimethylformamide, in the presence of a base, e.g. potassium carbonate.

The reaction temperature is in general from 20° to 130° C.

In a process variant, the benzyl compounds III (where L is chlorine or bromine) are reacted with the alkali metal salts, preferably the sodium or potassium salts, of the sulfonic acids in the inert solvent.

The ortho-substituted benzyl esters of cyclopropanecarboxylic acids I are suitable as fungicides and for controlling pests.

The ortho-substituted benzyl esters of cyclopropanecarboxylic acids I have excellent activity against a broad spectrum of phytopathogenic fungi, in particular from the class consisting of the Ascomycetes and Basidiomycetes. Some of them have systemic activity and can be used as foliage and soil fungicides.

They are particularly important for controlling a large number of fungi on various crops, such as wheat, rye, barley, oats, rice, corn, grass, cotton, soybean, coffee, sugar cane, grapevines, fruit trees, ornamentals and vegetable plants, such as cucumbers, beans and cucurbitaceae, and on the seeds of these plants.

They are particularly suitable for controlling the following plant diseases:

Erysiphe graminis (powdery mildew) in cereals,
Erysiphe cichoracearum and Sphaerotheca fuliginea on cucurbitaceae,
Podosphaera leucotricha on apples,
Uncinula necator on grapevines,
Puccinia species on cereals,
Rhizoctonia species on cotton and lawns,
Ustilago species on cereals and sugar cane,
Venturia inaequalis (scab) on apples, Helminthosporium species on cereals,
Septoria nodorum on wheat,
Botrytis cinerea (gray mold) on strawberries and grapevines,
Cercospora arachidicola on peanuts,
Pseudocercosporella herpotrichoides on wheat and barley,
Pyricularia oryzae on rice,
Phytophthora infestans on potatoes and tomatoes,
Fusarium and Verticillium species on various plants,
Plasmopara viticola on grapevines and
Alternaria species on vegetables and fruits.

The compounds are used for treating the fungi or the plants, seeds or materials to be protected from fungal attack or the soil with a fungicidal amount of the active ingredients. Application is effected before or after infection of the materials, plants or seeds by the fungi.

The ortho-substituted benzyl esters of cyclopropanecarboxylic acids I are furthermore suitable for controlling pests from the class consisting of insects, arachnids and nematodes. They can be used as pesticides in crop protection, in the hygiene and veterinary sectors and for the protection of stored materials.

The insect pests include, from the order of the butterflies (Lepidoptera), for example Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis;

from the order of the beetles (Coleoptera), for example Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibiails, Conoderus vespertinus, Crioceris asparagi, Diabrotica longicornis, Diabrotica 12-punctata, Diabrotica virgifera, Eiplachna varivestis, Epitrix hirtipennis, Eutinobothrus brasiliensis, Hylobius abietis, Hypera brunneipennis, HArpera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia Japonica, Sitona lineatus and Sitophilus granaria.;

from the order of the Diptera, for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella firt, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* from the order of the Thysanoptera, for example *Franklinleila fusca, Franklinleila occidentalis, Franklinleila tritici, Scirtothrips citri, Thrips oryzae, Thrips palmi* and *Thrips tabaci;* from the order of the Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta;* from the order of the Heteroptera, for example *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor;* from the order of the Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mall, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii;* from the order of the Isoptera, for example *Calotermes flavicollis, Leucotermes flavipes, Reticulitermes lucifugus* and *Termes natalensis;* from the order of the Orthoptera, for example *Acheta domestica, Blatta orientalis, Blattella germanica, Forficula auricularia, Gryllotalpa gryllotalpa, Locusta migratoria, Melanoplus birittatus, Melanoplus femurrubrum, Melanoplus mexicanus, Melanoplus sanguinipes, Melanoplus spretus, Nomadacris septemfasciata, Priplaneta americana, Schistocerca americana, Schistocerca peregrina, Stauronotus maroccanus* and *Tachycines asynamorus;* from the class of the Arachnoidea, for example Acarina, such as *Amhlyomma americanum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae;* from the class of the nematodes, for example root gall nematodes, e.g. *Meloidogyne hapla, Meloidogyne incognita* and *Meloidogyne Javanica,* cyst-forming nematodes, e.g. *Globodera rostochiensis, Heterodera avenae, Heterodera glycinae, Heterodera schatii, Heterodera triflolii,* and stem and leaf borers, e.g. *Belonolaimus lonicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients can be converted into the conventional formulations, such as solutions, emulsions, suspensions, dusts, powders, pastes and granules. The application forms depend on the intended uses; they should in any case ensure fine and uniform distribution of the ortho-substituted benzyl ester of a cyclopropanecarboxylic acid. The formulations are prepared in a known manner, for example by extending the active ingredient with the solvents and/or carriers, if required with the use of emulsifiers and dispersants; where water is used as a diluent, other organic solvents may also be employed as auxiliary solvents.

For the preparation of directly sprayable solutions, emulsions, pastes or oil dispersions, mineral oil fractions having a medium to high boiling point, such as kerosene or diesel oil, and coal tar oils and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone and strongly polar solvents, e.g. dimethylformamide, dimethyl sulfoxide, N-methylpyrrolidone and water, are suitable.

Aqueous application forms can be prepared from emulsion concentrates, pastes or wettable powders (spray powders, oil dispersions) by adding water. For the preparation of emulsions, pastes or oil dispersions, the substances, as such or dissolved in an oil or solvent, can be homogenized in water by means of wetting agents, adhesives, dispersants or emulsifiers. However, concentrates which consist of active substance, wetting agents, adhesives, dispersants or emulsifiers and possibly a solvent or oil and which are suitable for dilution with water can also be prepared.

Suitable surfactants are alkali metal, alkaline earth metal and ammonium salts of ligninsulfonic acid, naphthalenesulfonic acid, phenolsulfonic acid and dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusting agents can be prepared by mixing or milling the active substances together with a solid carrier.

The formulations contain in general from 0.01 to 95, preferably from 0.1 to 90, % by weight of the active ingredient. The active ingredients are used in a purity of from 90 to 100%, preferably from 95 to 100% (according to NMR spectrum).

Examples of such formulations are:

I. a solution of 90 parts by weight of compound No. 3 and 10 parts by weight of N-methyl-α-pyrrolidone, which solution is suitable for use in the form of very small drops;

II. a mixture of 20 parts by weight of compound No. 4, 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid, 5 parts by weight of the adduct of 40 moles of ethylene oxide with 1 mole of castor oil; by finely distributing the solution in water, a dispersion is obtained;

III. an aqueous dispersion of 20 parts by weight of compound No. 5, 40 parts by weight of cyclohexanone, 30 parts by weight of isobutanol, 20 parts by weight of the adduct of 40 moles of ethylene oxide with 1 mole of castor oil;

IV. an aqueous dispersion of 20 parts by weight of compound No. 6, 25 parts by weight of cyclohexanol, 65 parts by weight of a mineral oil fraction boiling within a range from 210° to 280° C. and 10 parts by weight of the adduct of 40 moles of ethylene oxide with 1 mole of castor oil;

V. a mixture milled in a hammer mill and consisting of 80 parts by weight of compound No. 7, 3 parts by weight of the sodium salt of diisobutylnaphthalene-α-sulfonic acid, 10 parts by weight of the sodium salt of ligninsulfonic acid obtained from a sulfite waste liquor and 7 parts by weight of silica gel powder; by finely distributing the mixture in water, a spray liquor is obtained;

VI. an intimate mixture of 3 parts by weight of compound No. 15 and 97 parts by weight of finely divided kaolin; this dusting agent contains 3% by weight of the active ingredient;

VII. an intimate mixture of 30 parts by weight of compound No. 103, 92 parts by weight of silica gel powder and 8 parts by weight of liquid paraffin, which was sprayed onto the surface of this silica gel; this formulation imparts good adhesion to the active ingredient;

VIII. a stable aqueous dispersion of 40 parts by weight of compound No. 109, 10 parts by weight of the sodium salt of a phenolsulfonic acid/urea/formaldehyde condensate, 2 parts by weight of silica gel and 48 parts by weight of water, which dispersion can be further diluted;

IX. a stable oily dispersion of 20 parts by weight of compound No. 177, 2 parts by weight of the calcium salt of dodecylbenzenesulfonic acid, 8 parts by weight of a fatty alcohol polyglycol ether, 20 parts by weight of the sodium salt of a phenolsulfonic acid/urea/formaldehyde condensate and 68 parts by weight of a paraffinic mineral oil.

Granules, for example coated, impregnated and homogeneous granules, can be prepared by binding the active ingredients to solid carriers. Examples of solid carriers are mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, e.g. ammonium sulfate, ammonium phosphate, ammonium nitrate and ureas, and vegetable products, such as cereal meal, ground bark, woodmeal and nutshell meal, cellulose and other solid carriers.

The active ingredient concentrations in the ready-to-use formulations can be varied within wide ranges.

Very generally, the agents contain from 0.0001 to 95, preferably from 0.01 to 90, % by weight of active ingredient.

Formulations containing more than 95% by weight of active ingredient can be successfully applied by the ultralow volume method (ULV), and it is even possible to use the active ingredient without additives.

In the case of fungicides, the application rates are from 0.02 to 3 kg of active ingredient per ha, depending on the type of effect desired. The novel compounds can also be used in material protection (wood preservation), for example against Paecilomyces variotii.

In seed treatment, amounts of active ingredient of from 0.001 to 50 g, preferably from 0.01 to 10 g, per kilogram of seed are generally required.

The application rate of active ingredient for controlling insects is from 0.02 to 10, preferably from 0.1 to 2.0, kg/ha under open air conditions.

The novel agents in these application forms may be present together with other active ingredients, for example with herbicides, insecticides, growth regulators, fungicides or fertilizers. These agents can be added to the novel agents in a weight ratio of from 1:10 to 10:1, if necessary also immediately before use (tank mix). Mixing with fungicides or insecticides results in an extension of the action spectrum in many cases.

The agents or the ready-to-use formulations prepared therefrom, such as solutions, emulsions, suspensions, powders, dusts, pastes or granules, are applied in a known manner, for example by spraying, atomizing, dusting, broadcasting, dressing or pouring.

PREPARATION EXAMPLES

Example 1 (Compound No. 3 in Table 1)

Methyl alpha-{2-[1-(n-propyl)-cyclopropylcarbonyloxymethyl]-phenyl}-beta-methoxyacrylate

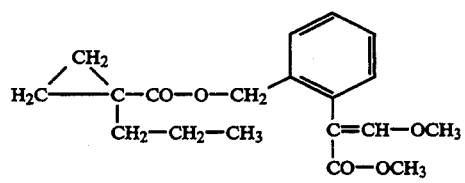

A solution of 3.5 g (27 mmol) of 1-n-propylcyclopropanecarboxylic acid and 1.5 g (27 mmol) of potassium hydroxide in 75 ml of ethanol was stirred for 2 hours at 20° C. Thereafter, the precipitated potassium salt was separated off, washed with 100 ml of diethyl ether and suspended in 50 ml of dimethylformamide. 5.7 g (20 mmol) of methyl alpha-(2-bromomethylphenyl)-betamethoxyacrylate were added to this suspension and the mixture was then heated for 2 hours at 90° C. After cooling to 20° C., the mixture was hydrolyzed with 50 ml of water. The product was then extracted with diethyl ether and isolated in a conventional manner. Purification was carried out by chromatography using silica gel as the adsorbent and cyclohexane as the mobile phase. Yield: 66%; mp.: 62°–64° C.

Intermediate 1a tert-Butyl 1-allylcyclopropanecarboxylate

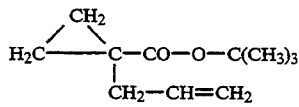

A solution of 34.1 g (0.24 mol) of tert-butyl cyclopropanecarboxylate in 25 ml of tetrahydrofuran was added dropwise at −70° C. to a mixture of 33.6 ml (0.24 mol) of diisopropylamine, 150 ml of a 1.5 molar solution of n-butyllithium in n-hexane ($\triangleq$ 0.24 mol of butyllithium) and 100 ml of tetrahydrofuran. Stirring was carried out for 3 hours at −70° C., after which a solution of 27.8 g (0.23 mol) of allyl bromide in 25 ml of tetrahydrofuran was added dropwise. Thereafter, the reaction mixture was stirred for a further 2 hours at −70° C. and then for 12 hours at 20° C. After hydrolysis with 50 ml of saturated aqueous ammonium chloride solution and after phase separation, the organic phase was worked up in a conventional manner to obtain the product. The crude product was purified by distillation. Yield: 61%, bp.: 86°–88° C. at 30 mbar; colorless oil.

Intermediate 1b tert-Butyl 1-n-propylcyclopropanecarboxylate

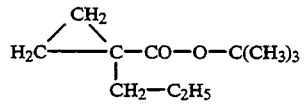

25.5 g (0.14 mol) of tert-butyl 1-allylcyclopropanecarboxylate, dissolved in 150 ml of tetrahydrofuran, were hydrogenated at 30° C. and at a hydrogen pressure of 10 bar, with the addition of 6 g of alumina which contained 0.5% by weight of palladium. After no further hydrogen was absorbed (constant pressure), the solids were filtered off and the filtrate was evaporated to dryness. The crude product was purified by distillation. Yield: 87%; bp.: 89° C. at 36 mbar; colorless oil.

Intermediate 1c 1-n-Propylcyclopropanecarboxylic acid

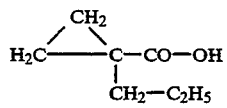

A stirred mixture of 21.0 g (0.11 mol) of tertbutyl 1-n-propylcyclopropanecarboxylate and 13.0 g (0.11 mol) of trifluoroacetic acid was refluxed for 3 hours and then added to 20 ml of dilute sodium hydroxide solution. After extraction of the byproducts with diethyl ether, the aqueous phase was acidified with dilute hydrochloric acid and again extracted with diethyl ether. This ether phase was then worked up in a conventional manner to obtain the product. Yield: 95%; colorless oil.

EXAMPLE 2 (compound No. 4 in Table 1)

2-[1-(n-Propyl)-cyclopropylcarbonyloxymethyl]-phenylglyoxylic acid methyl ester O-methyloxime

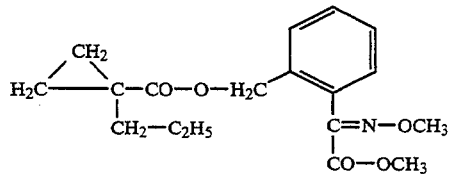

A mixture of 2.8 g (22 mmol) of 1-n-propylcyclopropanecarboxylic acid (prepared according to Example 1c), 1.3 g (23 mmol) of potassium hydroxide and 50 ml of ethanol was stirred for 1 hour at 20° C. Thereafter, the precipitated potassium salt was separated off, washed with 50 ml of diethyl ether and suspended in 100 ml of dimethylformamide. 4.3 g (15 mmol) of 2-(bromomethyl)-phenylglyoxylic acid methyl ester O-methyloxime were added to this suspension and the mixture was then heated for 2 hours at 100° C. After cooling to 20° C., the mixture was hydrolyzed with 50 ml of water and worked up similarly to Example 1 to obtain the product. Yield: 38%; mp. 56°–59° C.; colorless crystals.

Example 3 (Compound No. 5 in Table 1)

Methyl alpha-{2-[1-(allyl)-cyclopropylcarbonyloxymethyl]-phenyl}-beta-methoxyacrylate

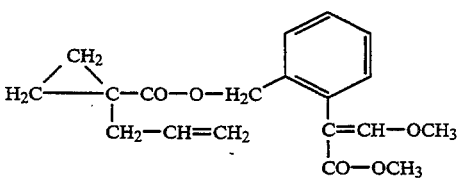

A solution of 4.5 g (36 mmol) of 1-allylcyclopropanecarboxylic acid and 2.2 g (39 mmol) of potassium hydroxide in 50 ml of ethanol was stirred for 2 hours at 20° C. and then evaporated down. The residue was covered with a layer of diethyl ether, after which the resulting precipitate was separated off and washed with diethyl ether. Subsequent reaction of the potassium salt of 1-allylcyclopropanecarboxylic acid in 50 ml of N-methylpyrrolidone with 8.5 g (30 mmol ) of methyl alpha- (2-bromomethylphenyl)-beta-methoxyacrylate and purification of the end product were carried out similarly to Example 1. Yield: 40%; colorless oil.

Intermediate 3a

1-Allylcyclopropanecarboxylic acid

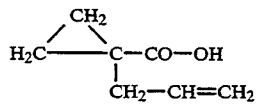

24.0 g (0.13 mol) of tert-butyl 1-allylcyclopropanecarboxylate (prepared according to Example 1a) were reacted with 14.9 g (0.13 mol) of trifluoroacetic acid similarly to Example 1c. Yield: 90%; colorless oil.

EXAMPLE 4 (Compound No. 6 in Table 1)

2-[1-(Allyl)-cyclopropylcarbonyloxymethyl]-phenylglyoxylic acid methyl ester O-methyloxime

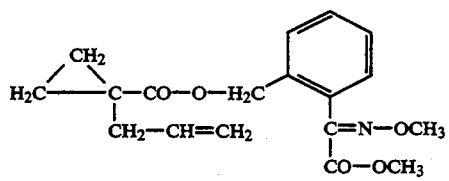

2.3 g (18 mmol) of 1-allylcyclopropanecarboxylic acid (prepared according to Example 1c) were converted with 1.1 g (20 mmol) of potassium hydroxide into the potassium salt of 1-allylcyclopropanecarboxylic acid similarly to Example 3, and said salt in 50 ml of dimethylformamide was reacted with 4.3 g (15 mmol) of 2-(bromomethyl)-phenylglyoxylic methyl ester O-methyloxime. Yields: 84%; colorless oil.

EXAMPLE 5 (Compound No. 7 in Table 1)

Methyl alpha-{2-[1-(trifluoromethyl)-cyclopropylcarbonyloxymethyl]-phenyl}-beta-methoxyacrylate

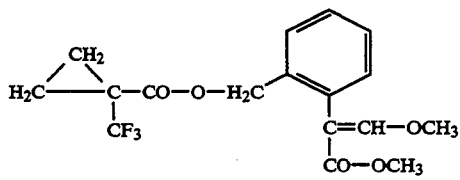

A solution of 10.0 g (55 mmol) of ethyl 1-trifluoromethylcyclopropanecarboxylate and 3.4 g (61 mmol) of potassium hydroxide in 150 ml of ethanol was stirred for 4 hours at 40° C. and then evaporated down. The residue was covered with a layer of diethyl ether, after which the resulting precipitate was separated off, washed with diethyl ether and suspended in 100 ml of dimethylformamide. 10.0 g (35 mmol) of methyl alpha-(2-bromo-methylphenyl)-beta-methoxyacrylate were added to this suspension and the mixture was then heated for 2 hours at 95° C. After cooling to 20° C., the mixture was hydrolyzed with 50 ml of water. The product was then extracted with diethyl ether and isolated in a conventional manner.

The oily crude product was covered with a layer of pentane and was crystallized by rubbing the wall of the vessel. Yield: 64%; mp.: 58°–60° C.; white crystals.

Intermediate 5a

Monoethyl cyclopropane-1,1-dicarboxylate

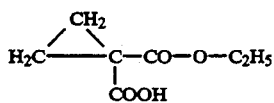

A solution of 53 g (285 mmol) of diethyl cyclopropane-1,1-dicarboxylate and 16.0 g (286 mmol) of potassium hydroxide in 300 ml of ethanol was stirred for 3 hours at 20° C. and then evaporated to dryness. The residue was dissolved in 100 ml of water, after which byproducts were extracted with 200 ml of methylene chloride. After the aqueous phase had been acidified to pH 2 with dilute hydrochloric acid, the product was extracted with 200 ml of methyl tert -butyl ether and isolated in a conventional manner. Purification was carried out by distillation. Yield: 83%; bp.: 99°–102° C. at 2.5 mbar; colorless oil.

Intermediate 5b

Ethyl 1-trifluoromethylcyclopropanecarboxylate

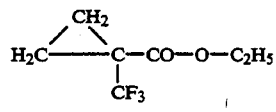

31.6 g (0.20 mol) of monoethyl cyclopropane-1,1-dicarboxylate, 126 g (1.16 mol) of sulfur tetrafluoride, 100 ml of dichloromethane and 1.5 g (75 mmol) of hydrogen fluoride were introduced at −70° C. into a 500 ml stirred autoclave which was lined with an alloy of 70% of nickel, 15% of chromium and 15% of molybdenum. The mixture was heated for 48 hours at 80° C. and the gaseous constituents were destroyed, after cooling the autoclave to 35° C., by passing them into a wash tower filled with potassium hydroxide. The residue was dissolved in 100 ml of dichloromethane. The solution was washed with 100 ml of saturated sodium bicarbonate solution, after which the organic phase was dried with sodium sulfate and potassium fluoride and was separated into the individual components by distillation. Yield: 76%; bp.: 141°–142° C.; oil.

Example 6 (Compound No. 8 in Table 1)

Methyl alpha-{2-[1-(trimethylsilyl)-cyclopropylcarbonyloxymethyl]-phenyl}-beta-methoxyacrylate

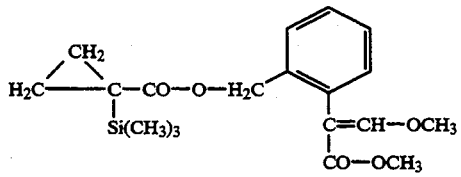

A procedure similar to Example 3 was used and 4.5 g (28mmol) of 1-trimethylsilylcyclopropanecarboxlic acid, dissolved in 80 ml of ethanol, were converted with 1.8 g (32 mmol) of potassium hydroxide into the potassium salt of trimethylsilylcyclopropanecarboxylic acid, and the latter was reacted with 5.7 g (20 mmol) of methyl alpha-(2-bromomethylphenyl)-beta-methoxyacrylate at 100° C. Yield: 62%; colorless oil.

Intermediate 6a

1-Trimethylsilylcyclopropanecarboxylic acid

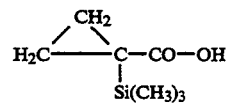

12.9 g (0.15 mol) of cyclopropanecarboxylic acid were added dropwise at −78° C. to a mixture of 42.0 ml (0.30 mol) of diisopropylamine, 200 ml of a 1.5 molar solution of n-butyllithium in n-hexane (=0.30 mol of butyllithium) and 150 ml of tetrahydrofuran, followed, after stirring for 30 minutes, by the dropwise addition of 81.3 g (0.75 mol) of trimethylchlorosilane at −78° C. Thereafter, the reaction mixture was stirred for a further 30 minutes at 0° C. and was heated to 20° C., 150 ml of methanol were then added and stirring was continued for a further 30 minutes. Hydrolysis was effected with water, after which the organic phase was separated off and evaporated down. Colorless crystals were obtained from the concentrated solution. Yields 38%; mp.: 124°-126° C.

Example 7 (Compound No. 11 in Table 1)

Methyl alpha-{2-[1-(ethoxycarbonyl)-cyclopropylcarbonyloxymethyl]-phenyl}-beta-methoxyacrylate

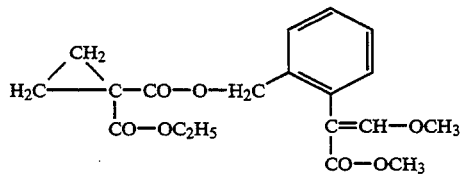

A method similar to Example 1 was used and 7.9 g (50 mmol) of monoethyl cyclopropane-1,1-dicarboxylate (prepared according to Example 5a) were converted with 2.8 g (50 mmol) of potassium hydroxide into the potassium salt of monomethyl cyclopropane-1,1-dicarboxylate, and said salt was then reacted with 10 g (35 mmol) of methyl alpha-[2-(bromomethyl)-phenyl]-beta-methoxyacrylate. The product was purified by distillation. Yield: 66%; bp.: 220° C. at 0.3 mbar; colorless oil.

Example 8 (Compound No. 17 in Table 1)

Methyl alpha-{2-[1-(2,6-difluorophenyl)-cyclopropylcarbonyloxymethyl]-phenyl}-beta-methoxyacrylate

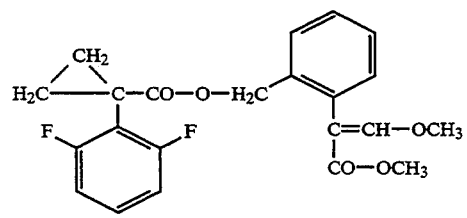

A method similar to Example 1 was used and 12.8 g (65 mmol) of 1-(2,6-difluorophenyl)-cyclopropanecarboxylic acid, dissolved in 60 ml of ethanol, were converted with 4.0 g (71 mmol) of potassium hydroxide into the potassium salt of 2,6-difluorophenylcyclopropanecarboxylic acid, and said salt was then reacted, at 100° C., in 100 ml of N-methylpyrrolidone, with 11.4 g (40 mmol) of methyl alpha-(2-bromomethylphenyl)-betamethoxyacrylate. The resulting oily product was covered with a layer of diisopropyl ether and was crystallized by rubbing the wall of the vessel. Yield: 86%; mp.: 108°-110° C.; white crystals.

Intermediate 8a 1-(2,6-Difluorophenyl)-cyclopropylnitrile

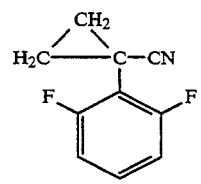

4.0 g of tetrabutylamonium chloride were added to a mixture of 30.6 g (0.20 mol) of 2,6-difluorobenzyl cyanide and 150.0 g (0.80 mol) of 1,2-dibromoethane, and 150 ml of 50% strength sodium hydroxide solution were then added dropwise. Stirring was carried out for 5 hours at 60° C., after which hydrolysis was effected with ice water. The product was extracted with diethyl ether from the resulting mixture and was isolated in a conventional manner. Purification was carried out by chromatography using silica gel as the adsorbent and cyclohexane as the mobile phase. Yield: 52%; mp.: 56°-58° C.; colorless crystals.

Intermediate 8b (2,6-Difluorophenyl)-cyclopropanecarboxylic acid

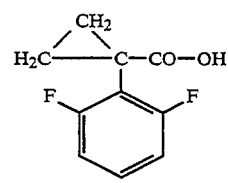

A suspension of 17.9 g (100 mmol) of 1-(2,6-difluorophenyl)-cyclopropylnitrile in a mixture of 60 ml of ice water and 40 ml of concentrated sulfuric acid was refluxed for 4 hours. The mixture was cooled to 25° C., after which the resulting precipitate was separated off, washed with water and dried. Yield=89%; mp.: 150°-153° C.; colorless crystals.

Example 9 (Compound No. 18 in Table 1)

2-[1-(2,6-Difluorophenyl)-cyclopropylcarbonyloxymethyl]-phenylglyoxylic acid methyl ester O-methyloxime

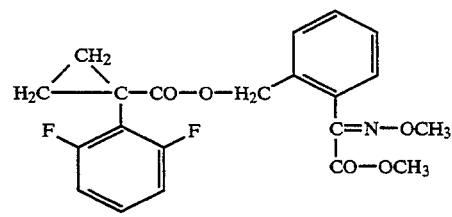

A method similar to Example 2 was used and 11.8 g (60 mmol) of 1-(2,6-difluorophenyl )-cyclopropanecarboxylic acid, prepared according to Example 8b and dissolved in 60 ml of ethanol, were converted with 3.6 g (64 mmol) of potassium hydroxide to the potassium salt of 2,6-difluorophenylcyclopropanecarboxylic acid, and said salt was then reacted, at 90° C., in 100 ml of N-methylpyrrolidone, with 13.3 g (47 mmol) of 2-(bromomethyl)phenylglyoxylic acid methyl ester O-methyloxime. The resulting oily product was covered with a layer of diisopropyl ether and was crystallized by rubbing the wall of the vessel. Yield: 85%; mp.: 122°–123° C.; white crystals.

Example 10 (Compound No. 29 in Table 1)

Methyl alpha-{2-[1-(4-fluorobenzyl)-cyclopropylcarbonyloxymethyl]-phenyl}-beta-methoxyacrylate

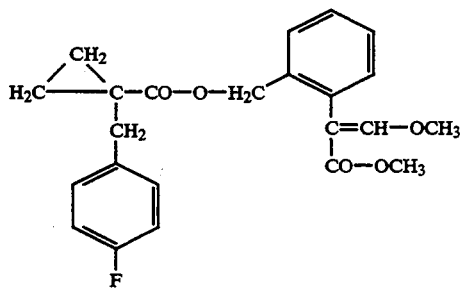

A method similar to Example 3 was used and 6.3 g (32 mmol) of 1-(4-fluorobenzyl)-cyclopropanecarboxylic acid were converted with 2.0 g (36 mmol) of potassium hydroxide into the potassium salt of fluorobenzylcyclopropanecarboxylic acid, and said salt was then reacted at 100° C. with 6.3 g (22 mmol) of methyl alpha-(2-bromomethylphenyl)-beta-methoxyacrylate. Yield: 54%; colorless oil.

Intermediate 10a tert-Butyl 1-(4-fluorobenzyl)-cyclopropanecarboxylate

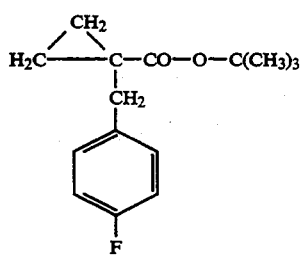

34.1 g (0.24 mol) of tert-butyl cyclopropanecarboxylate were converted into a lithium complex similarly to Intermediate 1a and this complex was reacted with 30.2 g (0.16 mol) of 4-fluorobenzyl bromide. Purification was carried out by chromatography using silica gel as the adsorbent and cyclohexane as the mobile phase. Yield: 72%; colorless oil.

Intermediate 10b 1-(4-Fluorobenzyl)-cyclopropanecarboxylic acid

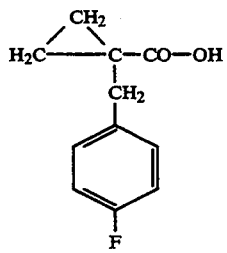

25.0 g (0.10 mol) of tert-butyl 1-(4-fluoro-benzyl)-cyclopropanecarboxylate (prepared according to Intermediate 10a) were reacted with 14.3 g (0.13 mol) of trifluoroacetic acid, similarly to Intermediate 1c. Yield: 90%; colorless oil.

Example 11 (Compound No. 30 in Table 1)

2-[1-(4-Fluorobenzyl)-cyclopropylcarbonyloxymethyl]phenylglyoxylic acid methyl ester O-methyloxime

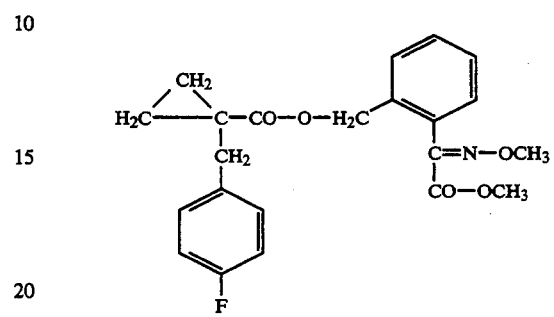

A method similar to Example 2 was used and 5.8 g (30 mmol) of 1-(4-fluorobenzyl)-cyclopropanecarboxylic acid (prepared according to Intermediate 10a) were converted with 1.8 g (32 mmol) of potassium hydroxide into the potassium salt of fluorobenzylcyclopropanecarboxylic acid, and said salt was then reacted with 6.3 g (22 mmol) of 2-(bromomethyl)-phenylglyoxylic acid methyl ester O-methyloxime. Purification was carried out by chromatography using silica gel as the adsorbent ant toluene as the mobile phase. Yield: 62%; colorless oil.

Example 12 (Compound No. 261 in Table 2)

Methyl alpha-[2-(1,2-dimethylcyclopropylcarbonyloxymethyl)-phenyl]-beta-methoxyacrylate

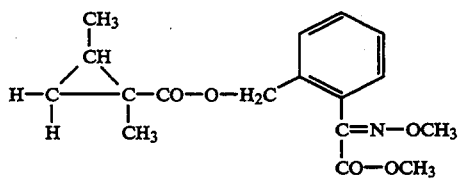

A stirred solution of 3.8 g (27 mmol) of ethyl 1,2-dimethylcyclopropanecarboxylate and 1.6 g (29 mmol) of potassium hydroxide in 50 ml of ethanol was refluxed for 8 hours and then evaporated down. The solution was covered with a layer of diethyl ether, after which the resulting precipitate was separated off and washed with diethyl ether. Subsequent reaction of the resulting potassium salt of dimethylcyclopropanecarboxylic acid in 60 ml of N-methylpyrrolidone, at 100° C., with 4.2 g (15 mmol) of methyl alpha-(2-bromomethylphenyl)-beta-methoxyacrylate and purification of the end product were carried out similarly to Example 1. Yield: 69%; colorless oil.

Intermediate 12a

Ethyl 1,2-dimethyl-3,3-dibromo-1-cyclopropanecarboxylate

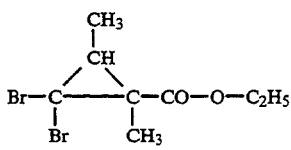

1 g (2 mmol) of hexadecyltributylphosphonium bromide and 50 ml of 50% strength by weight aqueous sodium hydroxide solution were added to a solution of g (0.25 mol) of ethyl (E)-2-methyl-2-butenoate in 80 32 ml of methylene chloride. Thereafter, 75.6 g (0.30 mol) of bromoform were added dropwise at 20° C. and the reaction mixture was stirred for 24 hours at 20° C. and for a further 8 hours at 50° C. 100 ml of water was then added to the mixture and the product was extracted with methylene chloride. The organic phase was worked up in a conventional manner to obtain the product. The crude product was purified by distillation. Yield: 37%; bp.: 102° C. 2 mbar; colorless oil.

Intermediate 12b

Ethyl 1,2-dimethylcyclopropanecarboxylate

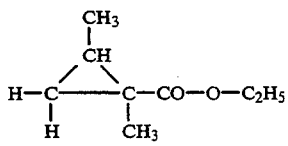

55 g (0.19 mol) of tributyltin hydride was slowly added dropwise at 20 °C. to a solution of 24 g (0.08 mol) of ethyl 1,2-dimethyl-3,3-dibromo-1-cyclopropanecarboxylate (prepared according to Intermediate 12a) in 50 ml of diethyl ether. Stirring was carried out for 12 hours at 20° C., after which the solvent was removed. The mixture was then stirred for a further 2 hours at 140° C. and was then separated by distillation at about 15 mbar (reduced pressure from a water pump). Yield: 76%; bp.: 54°–56° C. at 15 mbar; colorless oil.

Example 13 (Compound No. 263 in Table 2)

Methyl alpha- [2- ( 1,2-dimethyl-3,3-dibromocyclopropylcarbonyloxymethyl) -phenyl ]-beta-methoxyacrylate

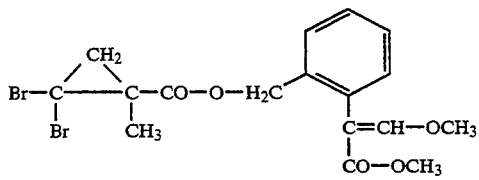

A solution of 11.0 g (36 mmol) of ethyl 1,2-dimethyl-3,3-dibromocyclopropanecarboxylate (prepared according to Intermediate 12a) and 2.2 g (40 mmol) of potassium hydroxide in 100 ml of ethanol was stirred for 6 hours at 60° C. and then evaporated down. The solution was covered with a layer of diethyl ether, after which the resulting precipitate was separated off and washed with diethyl ether. Subsequent reaction of the resulting potassium salt of dimethyldibromocyclopropanecarboxylic acid in 60 ml of N-methylpyrrolidone with 5.1 g (18 mmol) of methyl alpha- ( 2-bromomethylphenyl ) -beta-methoxyacrylate was carried out similarly to Example 1. After hydrolysis of the reaction mixture, the product was extracted with methyl tert-butyl ether and was isolated and purified similarly to Example 1. Yield: 32% colorless oil.

The physical data of the end products I are shown in Tables 1 to 4 below, which list further compounds which were prepared, or can be prepared, by the same methods.

TABLE 1

![Structure: H₂C—CH₂ / H₂C—C(CO—O—H₂C)(R¹), phenyl ring with C=X—OCH₃ and CO—OCH₃ groups]

| No. | R¹ | X | Config.*) | Physical data (NMR in CDCl₃ [ppm]; TMS as standard) |
|-----|-----|-----|-----|-----|
| 1 | H₃C—CH₂— | CH | | |
| 2 | H₃C—CH₂— | N | | |
| 3 | H₃C—CH₂—CH₂— | CH | E | 62-64° C.; NMR: 0.68(m, 2H); 0.89(t, 3H); 1.20(m, 2H); 1.51(m, 4H); 3.68(s, 3H); 3.79(s, 3H); 5.00(s, 2H); 7.13-7.41(m, 4H); 7.57(s, 1H). |
| 4 | H₃C—CH₂—CH₂— | N | E | 56-59° C.; NMR: 0.68(m, 2H); 0.87(t, 3H); 1.17(m, 2H); 1.47(m, 4H); 3.87(s, 3H); 4.05(s, 3H); 4.95(s, 2H); 7.13-7.45(m, 4H). |
| 5 | H₂C=CH—CH₂— | CH | E | oil; NMR: 0.76(m, 2H); 1.24(m, 2H); 2.35(d, 2H); 2.69(s, 3H); 3.80(s, 3H); 5.00(s, 2H); 5.04(d, 2H); 5.85(m, 1H); 7.13-7.43(m, 4H); 7.59(s, 1H). |
| 6 | H₂C=CH—CH₂— | N | E | oil; NMR: 0.73(m, 2H); 1.20(m, 2H); 2.32(d, 2H); 3.88(s, 3H); 4.03(s, 3H); 4.98(2s, 2H); 5.05(d, 2H); 5.83(m, 1H); 7.15-7.47(m, 4H). |
| 7 | CF₃— | CH | E | 58-60° C.; NMR: 1.27(m, 2H); 1.40(m, 2H); 3.63(s, 3H); 3.70(s, 3H); 5.10(s, 2H); 7.10-7.40(m, 4H); 7.53(s, 1H). |
| 8 | (CH₃)₃Si— | CH | E | oil; NMR: 0.03(s, 9H); 0.76(m, 2H); 1.19(m, 2H); 3.70(s, 3H); 3.80(s, 3H); 4.99(s, 2H); 7.13-7.44(m, 4H); 7.57(s, 1H). |
| 9 | CN— | CH | E | 91-92° C.; NMR: 1.60(m, 2H); 1.67(m, 2H); 3.70(s, 3H); 3.84(s, 3H); 7.12-7.50(m, 4H); 7.60(s, 1H). |
| 10 | CN— | N | | |
| 11 | H₃C—CH₂—O—C(O)— | CH | E | oil; NMR: 1.24(t, 3H); 1.44(s, 4H); 3.69(s, 3H); 3.80(s, 3H); 4.16(q, 4H); 5.07(s, 1H); 7.13-7.51(m, 4H); 7.59(s, 1H). |
| 12 | H₃C—CH₂—O—C(O)— | N | | |
| 13 | 2-Br—C₆H₄— | CH | E | 122-123° C.; NMR: 1.22(m, 2H); 1.75(m, 2H); 3.67(s, 3H); 3.78(s, 3H); 5.00(s, 2H); 7.07-7.60(m, 8H); 7.53(s, 1H). |
| 14 | 2,4-F₂—C₆H₃— | N | E | 106-107° C.; NMR: 1.20(m, 2H); 1.76(m, 2H); 3.83(s, 3H); 4.00(s, 3H); 4.96(s, 2H); 7.10-7.60(m, 8H). |
| 15 | 2,4-F₂—C₆H₃— | CH | E | 83-84° C.; NMR: 1.19(m, 2H); 1.65(s, 2H); 3.70(s, 3H); 3.82(s, 3H); 5.00(s, 2H); 6.77-7.31(m, 7H); 7.57(s, 1H). |
| 16 | 2,6-F₂—C₆H₃— | N | | |
| 17 | 2,6-F₂—C₆H₃— | CH | E | 108-110° C.; NMR: 1.25(m, 2H); 1.77(m, 2H); 3.67(s, 3H); 3.80(s, 3H); 5.00(s, 2H); 6.84-7.28(m, 7H); 7.56(s, 1H). |
| 18 | 2,6-F₂—C₆H₃— | N | E | 122-123° C.; NMR: 1.27(m, 2H); 1.73(m, 2H); 3.87(s, 3H); 4.03(s, 3H); 4.97(s, 2H); 6.82-7.37(m, 7H). |
| 19 | 2-F-6-Cl—C₆H₃— | CH | E | 126-127° C.; NMR: 1.28(m, 2H); 1.80(m, 2H); 3.67(s, 3H); 3.80(s, 3H); 5.00(s, 2H); 7.92-7.25(m, 7H); 7.53(s, 1H). |
| 20 | 2-F-6-Cl—C₆H₃— | N | E | 89-90° C. |
| 21 | 2,3,6-Cl₃—C₆H₂— | CH | E | oil; NMR: 1.37(m, 2H); 1.96(s, 2H); 3.68(s, 3H); 3.80(s, 3H); 5.00(s, 2H); 7.09-7.39(m, 6H); 7.57(s, 1H). |
| 22 | 2,3,6-Cl₃—C₆H₂— | N | | |
| 23 | C₆H₅—CH₂— | CH | E | oil; NMR: 0.78(m, 2H); 1.27(m, 2H); 2.98(s, 2H); 3.63(s, 3H); 3.70(s, 3H); 4.79(s, 2H); 7.08-7.27(m, 9H); 7.52(s, 1H). |
| 24 | C₆H₅—CH₂— | N | E | oil; NMR: 0.77(m, 2H); 1.23(m, 2H); 2.98(s, 2H); 3.83(s, 3H); 4.00(s, 3H); 4.93(s, 2H); 7.12-7.37(m, 9H). |

TABLE 1-continued

Structure:

$$H_2C\underset{CH_2}{\diagup}\hspace{-1em}\diagdown C-CO-O-H_2C-\text{(2-substituted phenyl)}-C=X-OCH_3 / CO-OCH_3$$

with $R^1$ on the cyclopropane carbon.

| No. | $R^1$ | X | Config.[*] | Physical data (NMR in CDCl$_3$ [ppm]; TMS as standard) |
|---|---|---|---|---|
| 25 | 2-F—C$_6$H$_4$—CH$_2$— | CH | | oil |
| 26 | 2-F—C$_6$H$_4$—CH$_2$— | N | E | oil |
| 27 | 3-F—C$_6$H$_4$—CH$_2$— | CH | E | oil; NMR: 0.80(m, 2H); 1.38(m, 2H); 2.94(s, 2H); 3.68(s, 3H); 3.74(s, 3H); 4.98(s, 2H); 6.89–7.30(m, 8H); 7.53(s, 1H). |
| 28 | 3-F—C$_6$H$_4$—CH$_2$— | N | E | |
| 29 | 4-F—C$_6$H$_4$—CH$_2$— | CH | E | oil; NMR: 0.75(m, 2H); 1.25(m, 2H); 2.93(s, 2H); 3.83(s, 3H); 4.00(s, 3H); 4.92(s, 2H); 6.83–6.37(m, 8H). |
| 30 | 4-F—C$_6$H$_4$—CH$_2$— | N | E | |
| 31 | 2-Cl—C$_6$H$_4$—CH$_2$— | CH | E | oil |
| 32 | 2-Cl—C$_6$H$_4$—CH$_2$— | N | E | oil |
| 33 | 3-Cl—C$_6$H$_4$—CH$_2$— | CH | E | oil |
| 34 | 3-Cl—C$_6$H$_4$—CH$_2$— | N | E | oil |
| 35 | 4-Cl—C$_6$H$_4$—CH$_2$— | CH | E | oil |
| 36 | 4-Cl—C$_6$H$_4$—CH$_2$— | N | | |
| 37 | 2-Br—C$_6$H$_4$—CH$_2$— | CH | | |
| 38 | 2-Br—C$_6$H$_4$—CH$_2$— | N | | |
| 39 | 3-Br—C$_6$H$_4$—CH$_2$— | CH | | |
| 40 | 3-Br—C$_6$H$_4$—CH$_2$— | N | | |
| 41 | 4-Br—C$_6$H$_4$—CH$_2$— | CH | E | oil |
| 42 | 4-Br—C$_6$H$_4$—CH$_2$— | N | E | oil |
| 43 | 2-CH$_3$—C$_6$H$_4$—CH$_2$— | CH | | |
| 44 | 2-CH$_3$—C$_6$H$_4$—CH$_2$— | N | | |
| 45 | 3-CH$_3$—C$_6$H$_4$—CH$_2$— | CH | E | oil |
| 46 | 3-CH$_3$—C$_6$H$_4$—CH$_2$— | N | E | oil |
| 47 | 4-CH$_3$—C$_6$H$_4$—CH$_2$— | CH | | |
| 48 | 4-CH$_3$—C$_6$H$_4$—CH$_2$— | N | | |
| 49 | 2-CH$_3$O—C$_6$H$_4$—CH$_2$— | CH | | |
| 50 | 2-CH$_3$O—C$_6$H$_4$—CH$_2$— | N | | |
| 51 | 3-CH$_3$O—C$_6$H$_4$—CH$_2$— | CH | | |
| 52 | 3-CH$_3$O—C$_6$H$_4$—CH$_2$— | N | | |
| 53 | 4-CH$_3$O—C$_6$H$_4$—CH$_2$— | CH | | |
| 54 | 4-CH$_3$O—C$_6$H$_4$—CH$_2$— | N | | |
| 55 | 2-C$_2$H$_5$O—C$_6$H$_4$—CH$_2$— | CH | | |
| 56 | 2-C$_2$H$_5$O—C$_6$H$_4$—CH$_2$— | N | | |
| 57 | 3-C$_2$H$_5$O—C$_6$H$_4$—CH$_2$— | CH | | |
| 58 | 3-C$_2$H$_5$O—C$_6$H$_4$—CH$_2$— | N | | |
| 59 | 4-C$_2$H$_5$O—C$_6$H$_4$—CH$_2$— | CH | | |
| 60 | 4-C$_2$H$_5$O—C$_6$H$_4$—CH$_2$— | N | | |
| 61 | 4-(CH$_3$)$_3$C—C$_6$H$_4$—CH$_2$— | CH | | |
| 62 | 4-(CH$_3$)$_3$C—C$_6$H$_4$—CH$_2$— | N | | |
| 63 | 2-CF$_3$—C$_6$H$_4$—CH$_2$— | CH | | |
| 64 | 2-CF$_3$—C$_6$H$_4$—CH$_2$— | N | | |

TABLE 1-continued

Structure:
H₂C—CH₂ group with C—CO—O—H₂C— connected to phenyl with C=X—OCH₃ and CO—OCH₃ substituents, R¹ on central C.

| No. | R¹ | X | Config.*) | Physical data (NMR in CDCl₃ [ppm]; TMS as standard) |
|---|---|---|---|---|
| 65 | 3-CF₃—C₆H₄—CH₂— | CH | | |
| 66 | 3-CF₃—C₆H₄—CH₂— | N | | |
| 67 | 4-CF₃—C₆H₄—CH₂— | CH | | |
| 68 | 4-CF₃—C₆H₄—CH₂— | N | | |
| 69 | 2,4-F₂—C₆H₃—CH₂— | CH | | |
| 70 | 2,4-F₂—C₆H₃—CH₂— | N | | |
| 71 | 2,6-F₂—C₆H₃—CH₂— | CH | | |
| 72 | 2,6-F₂—C₆H₃—CH₂— | N | | |
| 73 | 2,4-Cl₂—C₆H₃—CH₂— | CH | | |
| 74 | 2,4-Cl₂—C₆H₃—CH₂— | N | | |
| 75 | 2,6-Cl₂—C₆H₃—CH₂— | CH | | |
| 76 | 2,6-Cl₂—C₆H₃—CH₂— | N | | |
| 77 | 2-F-6-Cl—C₆H₃—CH₂— | CH | | |
| 78 | 2-F-6-Cl—C₆H₃—CH₂— | N | | |
| 79 | 3,4-Cl₂—C₆H₃—CH₂— | CH | | |
| 80 | 3,4-Cl₂—C₆H₃—CH₂— | N | | |
| 81 | 2,3,6-Cl₃—C₆H₂—CH₂— | CH | | |
| 82 | 2,3,6-Cl₃—C₆H₂—CH₂— | N | | |
| 83 | 2,4-(CH₃)₂—C₆H₃—CH₂— | CH | | |
| 84 | 2,4-(CH₃)₂—C₆H₃—CH₂— | N | | |
| 85 | 2,6-(CH₃)₂—C₆H₃—CH₂— | CH | | |
| 86 | 2,6-(CH₃)₂—C₆H₃—CH₂— | N | | |
| 87 | 3,4-(CH₃)₂—C₆H₃—CH₂— | CH | | |
| 88 | 3,4-(CH₃)₂—C₆H₃—CH₂— | N | | |
| 89 | 2,4-(CH₃O)₂—C₆H₃—CH₂— | CH | | |
| 90 | 2,4-(CH₃O)₂—C₆H₃—CH₂— | N | | |
| 91 | 2,6-(CH₃O)₂—C₆H₃—CH₂— | CH | | |
| 92 | 2,6-(CH₃O)₂—C₆H₃—CH₂— | N | | |
| 93 | 3,4-(CH₃O)₂—C₆H₃—CH₂— | CH | | |
| 94 | 3,4-(CH₃O)₂—C₆H₃—CH₂— | N | | |
| 95 | 3,4-(C₂H₅O)₂—C₆H₃—CH₂— | CH | | |
| 96 | 3,4-(C₂H₅O)₂—C₆H₃—CH₂— | N | | |
| 97 | C₆H₅—CH₂—CH₂— | CH | | |
| 98 | C₆H₅—CH₂—CH₂— | N | | |
| 99 | 2-F—C₆H₄—CH₂CH₂—CH₂— | CH | | |
| 100 | 2-F—C₆H₄—CH₂CH₂—CH₂— | N | | |
| 101 | 3-F—C₆H₄—CH₂CH₂—CH₂— | CH | | |
| 102 | 3-F—C₆H₄—CH₂CH₂—CH₂— | N | | |
| 103 | 4-F—C₆H₄—CH₂CH₂—CH₂— | CH | E | oil; NMR: 0.67(m, 2H); 1.20(m, 2H); 1.53(m, 2H); 1.75(m, 2H); 2.55(m, 2H); 3.67(s, 3H); 3.80(s, 3H); 5.00(s, 2H); 6.90-7.38(m, 8H); 7.58(s, 1H). |
| 104 | 4-F—C₆H₄—CH₂CH₂—CH₂— | N | E | oil; NMR: 0.67(m, 2H); 1.18(m, 2H); 1.53(m, 2H); 1.73(m, 2H); |

TABLE 1-continued

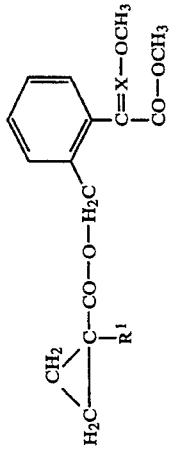

| No. | R¹ | X | Config.*) | Physical data (NMR in CDCl$_3$ [ppm]; TMS as standard) |
|---|---|---|---|---|
| 105 | 2-Cl—C$_6$H$_4$—CH$_2$CH$_2$—CH$_2$— | CH | | 2.55(m, 2H); 3.85(s, 3H); 4.02(s, 3H); 4.95(s, 2H); 6.88–7.40(m, 8H). |
| 106 | 2-Cl—C$_6$H$_4$—CH$_2$CH$_2$—CH$_2$— | N | | |
| 107 | 3-Cl—C$_6$H$_4$—CH$_2$CH$_2$—CH$_2$— | CH | | |
| 108 | 3-Cl—C$_6$H$_4$—CH$_2$CH$_2$—CH$_2$— | N | E | oil |
| 109 | 4-Cl—C$_6$H$_4$—CH$_2$CH$_2$—CH$_2$— | CH | | |
| 110 | 4-Cl—C$_6$H$_4$—CH$_2$CH$_2$—CH$_2$— | N | E | oil |
| 111 | 2-Br—C$_6$H$_4$—CH$_2$—CH$_2$—CH$_2$— | CH | | |
| 112 | 2-Br—C$_6$H$_4$—CH$_2$—CH$_2$—CH$_2$— | N | | |
| 113 | 3-Br—C$_6$H$_4$—CH$_2$—CH$_2$—CH$_2$— | CH | | |
| 114 | 3-Br—C$_6$H$_4$—CH$_2$—CH$_2$—CH$_2$— | N | | |
| 115 | 4-Br—C$_6$H$_4$—CH$_2$—CH$_2$—CH$_2$— | CH | | |
| 116 | 4-Br—C$_6$H$_4$—CH$_2$—CH$_2$—CH$_2$— | N | | |
| 117 | 2-CH$_3$—C$_6$H$_4$—CH$_2$—CH$_2$—CH$_2$— | CH | | |
| 118 | 2-CH$_3$—C$_6$H$_4$—CH$_2$—CH$_2$—CH$_2$— | N | | |
| 119 | 3-CH$_3$—C$_6$H$_4$—CH$_2$—CH$_2$—CH$_2$— | CH | | |
| 120 | 3-CH$_3$—C$_6$H$_4$—CH$_2$—CH$_2$—CH$_2$— | N | | |
| 121 | 4-CH$_3$—C$_6$H$_4$—CH$_2$—CH$_2$—CH$_2$— | CH | | |
| 122 | 4-CH$_3$—C$_6$H$_4$—CH$_2$—CH$_2$—CH$_2$— | N | | |
| 123 | 2-CH$_3$O—C$_6$H$_4$—CH$_2$—CH$_2$—CH$_2$— | CH | | |
| 124 | 2-CH$_3$O—C$_6$H$_4$—CH$_2$—CH$_2$—CH$_2$— | N | | |
| 125 | 3-CH$_3$O—C$_6$H$_4$—CH$_2$—CH$_2$—CH$_2$— | CH | | |
| 126 | 3-CH$_3$O—C$_6$H$_4$—CH$_2$—CH$_2$—CH$_2$— | N | | |
| 127 | 4-CH$_3$O—C$_6$H$_4$—CH$_2$—CH$_2$—CH$_2$— | CH | | |
| 128 | 4-CH$_3$O—C$_6$H$_4$—CH$_2$—CH$_2$—CH$_2$— | N | | |
| 129 | 2-C$_2$H$_5$O—C$_6$H$_4$—CH$_2$—CH$_2$—CH$_2$— | CH | | |
| 130 | 2-C$_2$H$_5$O—C$_6$H$_4$—CH$_2$—CH$_2$—CH$_2$— | N | | |
| 131 | 3-C$_2$H$_5$O—C$_6$H$_4$—CH$_2$—CH$_2$—CH$_2$— | CH | | |
| 132 | 3-C$_2$H$_5$O—C$_6$H$_4$—CH$_2$—CH$_2$—CH$_2$— | N | | |
| 133 | 4-C$_2$H$_5$O—C$_6$H$_4$—CH$_2$—CH$_2$—CH$_2$— | CH | | |
| 134 | 4-C$_2$H$_5$O—C$_6$H$_4$—CH$_2$—CH$_2$—CH$_2$— | N | | |
| 135 | 4-(CH$_3$)$_3$C—C$_6$H$_4$—CH$_2$—CH$_2$—CH$_2$— | CH | | |
| 136 | 4-(CH$_3$)$_3$C—C$_6$H$_4$—CH$_2$—CH$_2$—CH$_2$— | N | | |
| 137 | 2-CF$_3$—C$_6$H$_4$—CH$_2$—CH$_2$—CH$_2$— | CH | | |
| 138 | 2-CF$_3$—C$_6$H$_4$—CH$_2$—CH$_2$—CH$_2$— | N | | |
| 139 | 3-CF$_3$—C$_6$H$_4$—CH$_2$—CH$_2$—CH$_2$— | CH | | |
| 140 | 3-CF$_3$—C$_6$H$_4$—CH$_2$—CH$_2$—CH$_2$— | N | | |
| 141 | 4-CF$_3$—C$_6$H$_4$—CH$_2$—CH$_2$—CH$_2$— | CH | | |
| 142 | 4-CF$_3$—C$_6$H$_4$—CH$_2$—CH$_2$—CH$_2$— | N | | |
| 143 | 2,4-F$_2$—C$_6$H$_3$—CH$_2$—CH$_2$—CH$_2$— | CH | | |
| 144 | 2,4-F$_2$—C$_6$H$_3$—CH$_2$—CH$_2$—CH$_2$— | N | | |
| 145 | 2,6-F$_2$—C$_6$H$_3$—CH$_2$—CH$_2$—CH$_2$— | CH | | |

TABLE 1-continued

Structure: H2C-CH2 cyclopropane with C-CO-O-H2C attached to R¹; phenyl ring with C=X-OCH3 and CO-OCH3 substituents.

| No. | R¹ | X | Config.*) | Physical data (NMR in CDCl₃ [ppm]; TMS as standard) |
|---|---|---|---|---|
| 146 | 2,6-F₂—C₆H₃—CH₂—CH₂—CH₂— | N | | |
| 147 | 2,4-Cl₂—C₆H₃—CH₂—CH₂—CH₂— | CH | | |
| 148 | 2,4-Cl₂—C₆H₃—CH₂—CH₂—CH₂— | N | | |
| 149 | 2,6-Cl₂—C₆H₃—CH₂—CH₂—CH₂— | CH | | |
| 150 | 2,6-Cl₂—C₆H₃—CH₂—CH₂—CH₂— | N | | |
| 151 | 2-F-6-Cl—C₆H₃—CH₂—CH₂—CH₂— | CH | | |
| 152 | 2-F-6-Cl—C₆H₃—CH₂—CH₂—CH₂— | N | | |
| 153 | 3,4-Cl₂—C₆H₃—CH₂—CH₂—CH₂— | CH | | |
| 154 | 3,4-Cl₂—C₆H₃—CH₂—CH₂—CH₂— | N | | |
| 155 | 2,3,6-Cl₃—C₆H₂—CH₂—CH₂—CH₂— | CH | | |
| 156 | 2,3,6-Cl₃—C₆H₂—CH₂—CH₂—CH₂— | N | | |
| 157 | 2,4-(CH₃)₂—C₆H₃—CH₂—CH₂—CH₂— | CH | | |
| 158 | 2,4-(CH₃)₂—C₆H₃—CH₂—CH₂—CH₂— | N | | |
| 159 | 2,6-(CH₃)₂—C₆H₃—CH₂—CH₂—CH₂— | CH | | |
| 160 | 2,6-(CH₃)₂—C₆H₃—CH₂—CH₂—CH₂— | N | | |
| 161 | 3,4-(CH₃)₂—C₆H₃—CH₂—CH₂—CH₂— | CH | | |
| 162 | 3,4-(CH₃)₂—C₆H₃—CH₂—CH₂—CH₂— | N | | |
| 163 | 2,4-(CH₃O)₂—C₆H₃—CH₂—CH₂—CH₂— | CH | | |
| 164 | 2,4-(CH₃O)₂—C₆H₃—CH₂—CH₂—CH₂— | N | | |
| 165 | 2,6-(CH₃O)₂—C₆H₃—CH₂—CH₂—CH₂— | CH | | |
| 166 | 2,6-(CH₃O)₂—C₆H₃—CH₂—CH₂—CH₂— | N | | |
| 167 | 3,4-(CH₃O)₂—C₆H₃—CH₂—CH₂—CH₂— | CH | | |
| 168 | 3,4-(CH₃O)₂—C₆H₃—CH₂—CH₂—CH₂— | N | | |
| 169 | 3,4-(C₂H₅O)₂—C₆H₃—CH₂—CH₂—CH₂— | CH | | |
| 170 | 3,4-(C₂H₅O)₂—C₆H₃—CH₂—CH₂—CH₂— | N | | |
| 171 | C₆H₅—CH=CH—CH₂— | CH | | |
| 172 | C₆H₅—CH=CH—CH₂— | N | | |
| 173 | 2-F—C₆H₄—CH=CH—CH₂— | CH | | |
| 174 | 2-F—C₆H₄—CH=CH—CH₂— | N | | |
| 175 | 3-F—C₆H₄—CH=CH—CH₂— | CH | | |
| 176 | 3-F—C₆H₄—CH=CH—CH₂— | N | | |
| 177 | E-4-F—C₆H₄—CH=CH—CH₂— | CH | E | oil; NMR: 0.77(m, 2H); 1.23(m, 2H); 2.45(d, 2H); 3.67(s, 3H); 3.77(s, 3H); 5.00(s, 2H); 6.18(m, 1H); 6.33(d, 1H); 6.92—7.42(m, 8H); 7.58(s, 1H). |
| 178 | E-4-F—C₆H₄—CH=CH—CH₂— | N | E | oil; NMR: 0.78(m, 2H); 1.23(m, 2H); 2.43(d, 2H); 3.83(s, 3H); 4.03(s, 3H); 5.00(s, 2H); 6.13(m, 1H); 6.33(d, 1H); 6.92—7.40(m, 8H). |
| 179 | 2-Cl—C₆H₄—CH=CH—CH₂— | CH | | |
| 180 | 2-Cl—C₆H₄—CH=CH—CH₂— | N | | |
| 181 | 3-Cl—C₆H₄—CH=CH—CH₂— | CH | | |
| 182 | 3-Cl—C₆H₄—CH=CH—CH₂— | N | | |
| 183 | E-4-Cl—C₆H₄—CH=CH—CH₂— | CH | E | oil |
| 184 | E-4-Cl—C₆H₄—CH=CH—CH₂— | N | E | oil |

TABLE 1-continued

[Structure: H₂C=CH₂–H₂C–C(R¹)–CO–O–H₂C–(phenyl)–C=X–OCH₃, CO–OCH₃]

| No. | R¹ | X | Config.* | Physical data (NMR in CDCl₃ [ppm]; TMS as standard) |
|-----|-----|-----|-----|-----|
| 185 | 2-Br—C₆H₄—CH=CH—CH₂— | CH | | |
| 186 | 2-Br—C₆H₄—CH=CH—CH₂— | N | | |
| 187 | 3-Br—C₆H₄—CH=CH—CH₂— | CH | | |
| 188 | 3-Br—C₆H₄—CH=CH—CH₂— | N | | |
| 189 | 4-Br—C₆H₄—CH=CH—CH₂— | CH | | |
| 190 | 4-Br—C₆H₄—CH=CH—CH₂— | N | | |
| 191 | 2-CH₃—C₆H₄—CH=CH—CH₂— | CH | | |
| 192 | 2-CH₃—C₆H₄—CH=CH—CH₂— | N | | |
| 193 | 3-CH₃—C₆H₄—CH=CH—CH₂— | CH | | |
| 194 | 3-CH₃—C₆H₄—CH=CH—CH₂— | N | | |
| 195 | 4-CH₃—C₆H₄—CH=CH—CH₂— | CH | | |
| 196 | 4-CH₃—C₆H₄—CH=CH—CH₂— | N | | |
| 197 | 2-CH₃O—C₆H₄—CH=CH—CH₂— | CH | | |
| 198 | 2-CH₃O—C₆H₄—CH=CH—CH₂— | N | | |
| 199 | 3-CH₃O—C₆H₄—CH=CH—CH₂— | CH | | |
| 200 | 3-CH₃O—C₆H₄—CH=CH—CH₂— | N | | |
| 201 | 4-CH₃O—C₆H₄—CH=CH—CH₂— | CH | | |
| 202 | 4-CH₃O—C₆H₄—CH=CH—CH₂— | N | | |
| 203 | 2-C₂H₅O—C₆H₄—CH=CH—CH₂— | CH | | |
| 204 | 2-C₂H₅O—C₆H₄—CH=CH—CH₂— | N | | |
| 205 | 3-C₂H₅O—C₆H₄—CH=CH—CH₂— | CH | | |
| 206 | 3-C₂H₅O—C₆H₄—CH=CH—CH₂— | N | | |
| 207 | 4-C₂H₅O—C₆H₄—CH=CH—CH₂— | CH | | |
| 208 | 4-C₂H₅O—C₆H₄—CH=CH—CH₂— | N | | |
| 209 | 4-(CH₃)₃C—C₆H₄—CH=CH—CH₂— | CH | | |
| 210 | 4-(CH₃)₃C—C₆H₄—CH=CH—CH₂— | N | | |
| 211 | 2-CF₃—C₆H₄—CH=CH—CH₂— | CH | | |
| 212 | 2-CF₃—C₆H₄—CH=CH—CH₂— | N | | |
| 213 | 3-CF₃—C₆H₄—CH=CH—CH₂— | CH | | |
| 214 | 3-CF₃—C₆H₄—CH=CH—CH₂— | N | | |
| 215 | 4-CF₃—C₆H₄—CH=CH—CH₂— | CH | | |
| 216 | 4-CF₃—C₆H₄—CH=CH—CH₂— | N | | |
| 217 | 2,4-F₂—C₆H₃—CH=CH—CH₂— | CH | | |
| 218 | 2,4-F₂—C₆H₃—CH=CH—CH₂— | N | | |
| 219 | 2,6-F₂—C₆H₃—CH=CH—CH₂— | CH | | |
| 220 | 2,6-F₂—C₆H₃—CH=CH—CH₂— | N | | |
| 221 | 2,4-Cl₂—C₆H₃—CH=CH—CH₂— | CH | | |
| 222 | 2,4-Cl₂—C₆H₃—CH=CH—CH₂— | N | | |
| 223 | 2,6-Cl₂—C₆H₃—CH=CH—CH₂— | CH | | |
| 224 | 2,6-Cl₂—C₆H₃—CH=CH—CH₂— | N | | |
| 225 | 2-F-6-Cl—C₆H₃—CH=CH—CH₂— | CH | | |
| 226 | 2-F-6-Cl—C₆H₃—CH=CH—CH₂— | N | | |

TABLE 1-continued

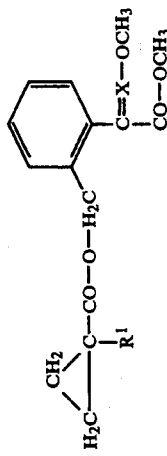

| No. | R¹ | X | Config.*) | Physical data (NMR in CDCl₃ [ppm]; TMS as standard) |
|---|---|---|---|---|
| 227 | 3,4-Cl₂—C₆H₃—CH=CH—CH₂— | CH | | |
| 228 | 3,4-Cl₂—C₆H₃—CH=CH—CH₂— | N | | |
| 229 | 2,3,6-Cl₃—C₆H₂—CH=CH—CH₂— | CH | | |
| 230 | 2,3,6-Cl₃—C₆H₂—CH=CH—CH₂— | N | | |
| 231 | 2,4-(CH₃)₂—C₆H₃—CH=CH—CH₂— | CH | | |
| 232 | 2,4-(CH₃)₂—C₆H₃—CH=CH—CH₂— | N | | |
| 233 | 2,6-(CH₃)₂—C₆H₃—CH=CH—CH₂— | CH | | |
| 234 | 2,6-(CH₃)₂—C₆H₃—CH=CH—CH₂— | N | | |
| 235 | 3,4-(CH₃)₂—C₆H₃—CH=CH—CH₂— | CH | | |
| 236 | 3,4-(CH₃)₂—C₆H₃—CH=CH—CH₂— | N | | |
| 237 | 2,4-(CH₃O)₂—C₆H₃—CH=CH—CH₂— | CH | | |
| 238 | 2,4-(CH₃O)₂—C₆H₃—CH=CH—CH₂— | N | | |
| 239 | 2,6-(CH₃O)₂—C₆H₃—CH=CH—CH₂— | CH | | |
| 240 | 2,6-(CH₃O)₂—C₆H₃—CH=CH—CH₂— | N | | |
| 241 | 3,4-(CH₃O)₂—C₆H₃—CH=CH—CH₂— | CH | | |
| 242 | 3,4-(CH₃O)₂—C₆H₃—CH=CH—CH₂— | N | | |
| 243 | 3,4-(C₂H₅O)₂—C₆H₃—CH=CH—CH₂— | CH | | |
| 244 | 3,4-(C₂H₅O)₂—C₆H₃—CH=CH—CH₂— | N | | |
| 245 | 3-Br—C₆H₄— | CH | | |
| 246 | 3-Br—C₆H₄— | N | | |
| 247 | 2-C₂H₅O—C₆H₄— | CH | | |
| 248 | 2-C₂H₅O—C₆H₄— | N | | |
| 249 | 3-C₂H₅O—C₆H₄— | CH | | |
| 250 | 3-C₂H₅O—C₆H₄— | N | | |
| 251 | 4-C₂H₅O—C₆H₄— | CH | | |
| 252 | 4-C₂H₅O—C₆H₄— | N | | |
| 253 | 2-CF₃—C₆H₃— | CH | | |
| 254 | 2-CF₃—C₆H₃— | N | | |
| 255 | 4-CF₃—C₆H₃— | CH | | |
| 256 | 4-CF₃—C₆H₃— | N | | |
| 257 | 2,4-(CH₃)₂—C₆H₃— | CH | | |
| 258 | 2,4-(CH₃)₂—C₆H₃— | N | | |
| 259 | 2,6-(CH₃)₂—C₆H₃— | CH | | |
| 260 | 2,6-(CH₃)₂—C₆H₃— | N | | |

*)Position of the substituents at the double bond —C(COOCH₃)=X—OCH₃

TABLE 2

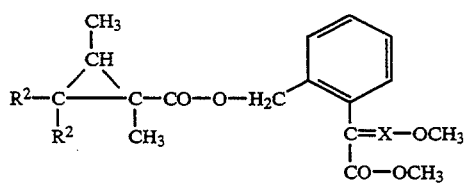

Ib

| No. | R² | X | Config.*) | Physical data (NMR in CDCl₃ [ppm]; TMS as standard) |
|---|---|---|---|---|
| 261 | H | CH | E; trans | oil; NMR: 0.32(m, 1H); 1.10(d, 3H); 1.23(s, 3H); 1.42(m, 2H); 3.67(s, 3H); 3.77(s, 3H); 4.98(s, 2H); 7.10–7.43(m, 4H); 7.55(s, 1H). |
| 262 | H | N | | |
| 263 | Br | CH | E; trans | oil; NMR: 1.15(d, 3H); 1.37(s, 3H); 2.40(m, 1H); 3.70(s, 3H); 3.80(s, 3H); 5.08(s, 2H); 7.13–7.50(m, 4H); 7.50(s, 1H). |
| 264 | Br | N | | |

*) Position of the substituents at the double bond —C(COOCH₃)=C—OCH₃ (E/Z) and position of the methyl group in the 2-position of the cyclopropane ring with respect to the benzyl ester group in the 1-position (cis/trans)

TABLE 3

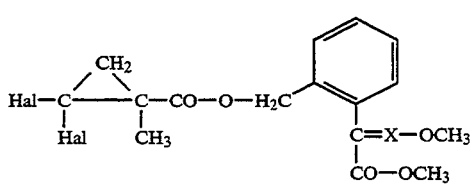

Ic

| No. | Hal | X | Config.*) | Physical data (NMR in CDCl₃ [ppm]; TMS as standard) |
|---|---|---|---|---|
| 265 | Br | CH | E | oil; NMR: 1.53(d, 1H); 1.56(s, 3H); 2.41(d, 1H); 3.71(s, 3H); 3.81(s, 3H); 5.08(s, 2H); 7.15–7.43(m, 4H); 7.60(s, 1H). |
| 266 | Br | N | | |

*) Position of the substituents at the double bond —C(COOCH₃)=X—OCH₃

TABLE 4

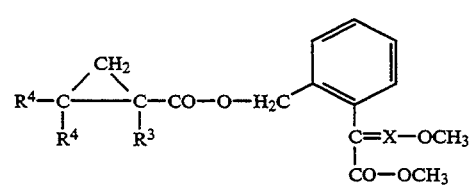

Id

| No. | R³ | R⁴ | X | Config.*) | Physical data (NMR in CDCl₃ [ppm]; TMS as standard) |
|---|---|---|---|---|---|
| 267 | C₆H₅— | CH₃ | CH | | |
| 268 | C₆H₅— | CH₃ | N | | |
| 269 | 2-F—C₆H₄— | CH₃ | CH | | |
| 270 | 2-F—C₆H₄— | CH₃ | N | | |
| 271 | 3-F—C₆H₄— | CH₃ | CH | | |
| 272 | 3-F—C₆H₄— | CH₃ | N | | |
| 273 | 4-F—C₆H₄— | CH₃ | CH | | |
| 274 | 4-F—C₆H₄— | CH₃ | N | | |
| 275 | 2-Cl—C₆H₄— | CH₃ | CH | | |
| 276 | 2-Cl—C₆H₄— | CH₃ | N | | |
| 277 | 3-Cl—C₆H₄— | CH₃ | CH | | |
| 278 | 3-Cl—C₆H₄— | CH₃ | N | | |
| 279 | 4-Cl—C₆H₄— | CH₃ | CH | | |
| 280 | 4-Cl—C₆H₄— | CH₃ | N | | |
| 281 | 2-Br—C₆H₄— | CH₃ | CH | | |
| 282 | 2-Br—C₆H₄— | CH₃ | N | | |
| 283 | 3-Br—C₆H₄— | CH₃ | CH | | |

TABLE 4-continued

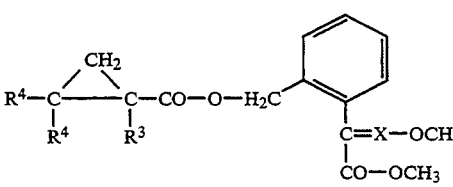

Id

| No. | R³ | R⁴ | X | Config.*) | Physical data (NMR in CDCl₃ [ppm]; TMS as standard) |
|---|---|---|---|---|---|
| 284 | 3-Br—C₆H₄— | CH₃ | N | | |
| 285 | 4-Br—C₆H₄— | CH₃ | CH | | |
| 286 | 4-Br—C₆H₄— | CH₃ | N | | |
| 287 | 2-CH₃—C₆H₄— | CH₃ | CH | | |
| 288 | 2-CH₃—C₆H₄— | CH₃ | N | | |
| 289 | 3-CH₃—C₆H₄— | CH₃ | CH | | |
| 290 | 3-CH₃—C₆H₄— | CH₃ | N | | |
| 291 | 4-CH₃—C₆H₄— | CH₃ | CH | | |
| 292 | 4-CH₃—C₆H₄— | CH₃ | N | | |
| 293 | 2-CH₃O—C₆H₄— | CH₃ | CH | | |
| 294 | 2-CH₃O—C₆H₄— | CH₃ | N | | |
| 295 | 3-CH₃O—C₆H₄— | CH₃ | CH | | |
| 296 | 3-CH₃O—C₆H₄— | CH₃ | N | | |
| 297 | 4-CH₃O—C₆H₄— | CH₃ | CH | | |
| 298 | 4-CH₃O—C₆H₄— | CH₃ | N | | |
| 299 | 2-C₂H₅O—C₆H₄— | CH₃ | CH | | |
| 300 | 2-C₂H₅O—C₆H₄— | CH₃ | N | | |
| 301 | 3-C₂H₅O—C₆H₄— | CH₃ | CH | | |
| 302 | 3-C₂H₅O—C₆H₄— | CH₃ | N | | |
| 303 | 4-C₂H₅O—C₆H₄— | CH₃ | CH | | |
| 304 | 4-C₂H₅O—C₆H₄— | CH₃ | N | | |
| 305 | 4-(CH₃)₃C—C₆H₄— | CH₃ | CH | | |
| 306 | 4-(CH₃)₃C—C₆H₄— | CH₃ | N | | |
| 307 | 2-CF₃—C₆H₄— | CH₃ | CH | | |
| 308 | 2-CF₃—C₆H₄— | CH₃ | N | | |
| 309 | 3-CF₃—C₆H₄— | CH₃ | CH | | |
| 310 | 3-CF₃—C₆H₄— | CH₃ | N | | |
| 311 | 4-CF₃—C₆H₄— | CH₃ | CH | | |
| 312 | 4-CF₃—C₆H₄— | CH₃ | N | | |
| 313 | 2,4-F₂—C₆H₃— | CH₃ | CH | | |
| 314 | 2,4-F₂—C₆H₃— | CH₃ | N | | |
| 315 | 2,6-F₂—C₆H₃— | CH₃ | CH | | |
| 316 | 2,6-F₂—C₆H₃— | CH₃ | N | | |
| 317 | 2,4-Cl₂—C₆H₃— | CH₃ | CH | | |
| 318 | 2,4-Cl₂—C₆H₃— | CH₃ | N | | |
| 319 | 2,6-Cl₂—C₆H₃— | CH₃ | CH | | |
| 320 | 2,6-Cl₂—C₆H₃— | CH₃ | N | | |
| 321 | 2-F-6-Cl—C₆H₃— | CH₃ | CH | | |
| 322 | 2-F-6-Cl—C₆H₃— | CH₃ | N | | |
| 323 | 3,4-Cl₂—C₆H₃— | CH₃ | CH | | |
| 324 | 3,4-Cl₂—C₆H₃— | CH₃ | N | | |
| 325 | 2,3,6-Cl₃—C₆H₂— | CH₃ | CH | | |
| 326 | 2,3,6-Cl₃—C₆H₂— | CH₃ | N | | |
| 327 | 2,4-(CH₃)₂—C₆H₃— | CH₃ | CH | | |
| 328 | 2,4-(CH₃)₂—C₆H₃— | CH₃ | N | | |
| 329 | 2,6-(CH₃)₂—C₆H₃— | CH₃ | CH | | |
| 330 | 2,6-(CH₃)₂—C₆H₃— | CH₃ | N | | |
| 331 | 3,4-(CH₃)₂—C₆H₃— | CH₃ | CH | | |
| 332 | 3,4-(CH₃)₂—C₆H₃— | CH₃ | N | | |
| 333 | 2,4-(CH₃O)₂—C₆H₃— | CH₃ | CH | | |
| 334 | 2,4-(CH₃O)₂—C₆H₃— | CH₃ | N | | |
| 335 | 2,6-(CH₃O)₂—C₆H₃— | CH₃ | CH | | |
| 336 | 2,6-(CH₃O)₂—C₆H₃— | CH₃ | N | | |
| 337 | 3,4-(CH₃O)₂—C₆H₃— | CH₃ | CH | | |
| 338 | 3,4-(CH₃O)₂—C₆H₃— | CH₃ | N | | |
| 339 | 3,4-(C₂H₅O)₂—C₆H₃— | CH₃ | CH | | |
| 340 | 3,4-(C₂H₅O)₂—C₆H₃— | CH₃ | N | | |
| 341 | C₆H₅— | Br | CH | | |
| 342 | C₆H₅— | Br | N | | |
| 343 | 2-F—C₆H₄— | Br | CH | | |
| 344 | 2-F—C₆H₄— | Br | N | | |
| 345 | 3-F—C₆H₄— | Br | CH | | |
| 346 | 3-F—C₆H₄— | Br | N | | |
| 347 | 4-F—C₆H₄— | Br | CH | | |
| 348 | 4-F—C₆H₄— | Br | N | | |
| 349 | 2-Cl—C₆H₄— | Br | CH | | |
| 350 | 2-Cl—C₆H₄— | Br | N | | |
| 351 | 3-Cl—C₆H₄— | Br | CH | | |

TABLE 4-continued

Id

R⁴—C(CH₂)(R⁴)—C(R³)—CO—O—H₂C—[C₆H₄]—C(=X—OCH₃)(CO—OCH₃)

| No. | R³ | R⁴ | X | Con-fig.*) | Physical data (NMR in CDCl₃ [ppm]; TMS as standard) |
|---|---|---|---|---|---|
| 352 | 3-Cl—C₆H₄— | | Br | N | |
| 353 | 4-Cl—C₆H₄— | | Br | CH | |
| 354 | 4-Cl—C₆H₄— | | Br | N | |
| 355 | 2-Br—C₆H₄— | | Br | CH | |
| 356 | 2-Br—C₆H₄— | | Br | N | |
| 357 | 3-Br—C₆H₄— | | Br | CH | |
| 358 | 3-Br—C₆H₄— | | Br | N | |
| 359 | 4-Br—C₆H₄— | | Br | CH | |
| 360 | 4-Br—C₆H₄— | | Br | N | |
| 361 | 2-CH₃—C₆H₄— | | Br | CH | |
| 362 | 2-CH₃—C₆H₄— | | Br | N | |
| 363 | 3-CH₃—C₆H₄— | | Br | CH | |
| 364 | 3-CH₃—C₆H₄— | | Br | N | |
| 365 | 4-CH₃—C₆H₄— | | Br | CH | |
| 366 | 4-CH₃—C₆H₄— | | Br | N | |
| 367 | 2-CH₃O—C₆H₄— | | Br | CH | |
| 368 | 2-CH₃O—C₆H₄— | | Br | N | |
| 369 | 3-CH₃O—C₆H₄— | | Br | CH | |
| 370 | 3-CH₃O—C₆H₄— | | Br | N | |
| 371 | 4-CH₃O—C₆H₄— | | Br | CH | |
| 372 | 4-CH₃O—C₆H₄— | | Br | N | |
| 373 | 2-C₂H₅O—C₆H₄— | | Br | CH | |
| 374 | 2-C₂H₅O—C₆H₄— | | Br | N | |
| 375 | 3-C₂H₅O—C₆H₄— | | Br | CH | |
| 376 | 3-C₂H₅O—C₆H₄— | | Br | N | |
| 377 | 4-C₂H₅O—C₆H₄— | | Br | CH | |
| 378 | 4-C₂H₅O—C₆H₄— | | Br | N | |
| 379 | 4-(CH₃)₃C—C₆H₄— | | Br | CH | |
| 380 | 4-(CH₃)₃C—C₆H₄— | | Br | N | |
| 381 | 2-CF₃—C₆H₄— | | Br | CH | |
| 382 | 2-CF₃—C₆H₄— | | Br | N | |
| 383 | 3-CF₃—C₆H₄— | | Br | CH | |
| 384 | 3-CF₃—C₆H₄— | | Br | N | |
| 385 | 4-CF₃—C₆H₄— | | Br | CH | |
| 386 | 4-CF₃—C₆H₄— | | Br | N | |
| 387 | 2,4-F₂—C₆H₃— | | Br | CH | |
| 388 | 2,4-F₂—C₆H₃— | | Br | N | |
| 389 | 2,6-F₂—C₆H₃— | | Br | CH | |
| 390 | 2,6-F₂—C₆H₃— | | Br | N | |
| 391 | 2,4-Cl₂—C₆H₃— | | Br | CH | |
| 392 | 2,4-Cl₂—C₆H₃— | | Br | N | |
| 393 | 2,6-Cl₂—C₆H₃— | | Br | CH | |
| 394 | 2,6-Cl₂—C₆H₃— | | Br | N | |
| 395 | 2-F-6-Cl—C₆H₃— | | Br | CH | |
| 396 | 2-F-6-Cl—C₆H₃— | | Br | N | |
| 397 | 3,4-Cl₂—C₆H₃— | | Br | CH | |
| 398 | 3,4-Cl₂—C₆H₃— | | Br | N | |
| 399 | 2,3,6-Cl₃—C₆H₂— | | Br | CH | |
| 400 | 2,3,6-Cl₃—C₆H₂— | | Br | N | |
| 401 | 2,4-(CH₃)₂—C₆H₃— | | Br | CH | |
| 402 | 2,4-(CH₃)₂—C₆H₃— | | Br | N | |
| 403 | 2,6-(CH₃)₂—C₆H₃— | | Br | CH | |
| 404 | 2,6-(CH₃)₂—C₆H₃— | | Br | N | |
| 405 | 3,4-(CH₃)₂—C₆H₃— | | Br | CH | |
| 406 | 3,4-(CH₃)₂—C₆H₃— | | Br | N | |
| 407 | 2,4-(CH₃O)₂—C₆H₃— | | Br | CH | |
| 408 | 2,4-(CH₃O)₂—C₆H₃— | | Br | N | |
| 409 | 2,6-(CH₃O)₂—C₆H₃— | | Br | CH | |
| 410 | 2,6-(CH₃O)₂—C₆H₃— | | Br | N | |
| 411 | 3,4-(CH₃O)₂—C₆H₃— | | Br | CH | |
| 412 | 3,4-(CH₃O)₂—C₆H₃— | | Br | N | |
| 413 | 3,4-(C₂H₅O)₂—C₆H₃— | | Br | CH | |
| 414 | 3,4-(C₂H₅O)₂—C₆H₃— | | Br | N | |

*)Position of the substituents at the double bond —C(COOCH₃)=X—OCH₃

USE EXAMPLES (FUNGICIDAL ACTIVITY)

The comparative substances used were

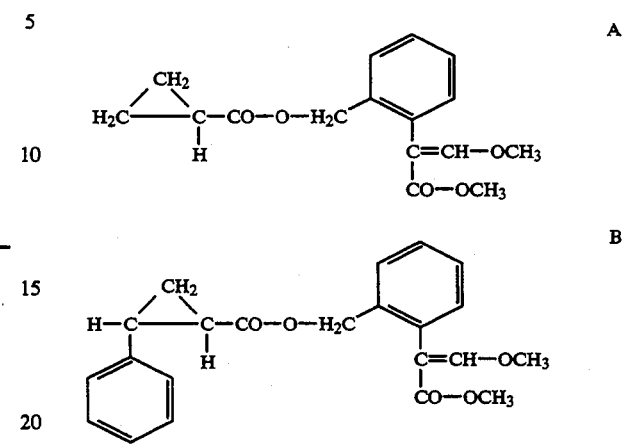

both of which are disclosed in DE 37 33 870 (compounds No. 71 and 364, both having an E configuration at the double bond).

Example 14

Activity against wheat mildew

Leaves of pot-grown wheat seedlings of the variety Frühgold were sprayed with 0.006 and 0.0015% strength aqueous active ingredient formulations which contained 80% of active ingredient (of the active ingredients according to Examples 3, 4, 5, 6, 7, 15, 18 and 261 in the Tables) and 20% of emulsifier, the percentages being based on dry material, and, 24 hours after the spray coating had dried on, were dusted with spores of wheat mildew (Erysiphe graminis var. tritici). The test plants were then placed in a greenhouse at from 20° to 22° C. and from 75 to 80% relative humidity. After 7 days, the extent of mildew development was evaluated.

Compared with the control experiment (no treatment, 70% fungal infestation) and the known comparative compounds A (40–50% fungal infestation) and B (50% fungal. infestation), the treated plants showed fungal infestation of only 0–15%.

Example 15

Activity against brown rust on wheat

Leaves of pot-grown wheat seedlings of the variety Frühgold were dusted with spores of brown rust (Puccinia recondita). The pots were then placed for 24 hours at from 20° to 22° C. in a chamber with from 90 to 95% relative humidity. During this time, the spores germinated and the germ tubes penetrated the leaf tissue. The infected plants were sprayed to run-off with a 0.025% strength aqueous spray liquor which contained 80% of active ingredient and 20% of emulsifier, the percentages being based on dry substance, and, after the spray coating had dried on, were placed in a greenhouse at from 20° to 22° C. and from 65 to 70% relative humidity. After 8 days, the extent of development of rust fungus on the leaves was evaluated.

The result shows that, when used as a 0.025% strength by weight spray liquor, active ingredients 3, 5, 7, 15, 24, 45, 103, 109, 110 and 177 have a better fungicidal action (97%) than the known comparative substances A (33%) and B (17%).

Example 16

Activity against *Pyricularia oryzae* (preventive treatment)

Leaves of pot-grown rice seedlings of the variety Bahia were sprayed to run-off with aqueous emulsions which contained 80% of active ingredient and 20% of emulsifier, the percentages being based on dry substance, and 24 hours later were infected with an aqueous spore suspension of *Pyricularia oryzae*. The test plants were then placed in conditioned chambers at from 20° to 24° C. and 95–99% relative humidity. After 6 days, the extent of fungal infestation was determined.

The result shows that, when used as a 0.05% strength by weight aqueous active ingredient formulation, active ingredients 3, 4, 5, 6, 8, 46, 103, 104, 109, 177, 183 and 261 have a much better fungicidal action (98%) than the known comparative substances A (0%) and B (50%).

USE EXAMPLES (INSECTICIDAL ACTIVITY)

The insecticidal action of ortho-substituted benzyl esters of cyclopropanecarboxylic acids I can be demonstrated by the following experiments:

The active ingredients were prepared as a 10% strength emulsion in a mixture of 70% by weight of cyclohexanol, 20% by weight of Nekanil ® LN (Lutensol PAP6, wetting agent having an emulsifying and dispersing effect and based on ethoxylated alkylphenols) and 10% by weight of Emulphor ® EL (Emulan ® EL, emulsifier based on ethoxylated fatty alcohols) and were diluted with water to give the desired concentration.

Example 17

Activity against *Tetranychus telarius* (red spider); contact action

Experiment 17 a

Bush beans which were contained in pots and had formed the second pair of secondary leaves and were severely infested with the spider mites were sprayed to run-off with aqueous active ingredient formulations of compound No. 29 which were of different concentrations. For this purpose, the plants were sprayed on a turntable from all sides with about 50 ml of the spray liquor. After 5 days in a greenhouse, the success of control was determined in % by means of a microscope (binocular).

At an active ingredient concentration of 200 ppm, compound No. 29 had a kill rate of from 80 to 90%.

Experiment 17 b (preventive treatment)

Bush beans which were contained in pots and had formed the second pair of secondary leaves were sprayed to run-off with active ingredient formulations of compound No. 29 which were of different concentrations, similarly to Experiment 17 a. After 24 hours, the plants were infected with pieces of leaf which were severely infested with spider mites.

After 12 days in a greenhouse, the success of control was determined in % by means of a microscope (binocular).

At an active ingredient concentration of 40 ppm, compound No. 29 had a kill rate of from 80 to 90%.

We claim:

1. An ortho-substituted benzyl ester of a cyclopropanecarboxylic acid of the formula I:

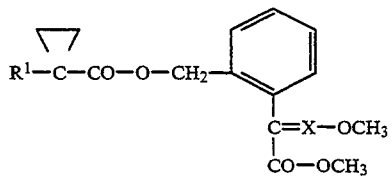

wherein

X is =N— or =CH—, and $R^1$ is cyano, trifluoromethyl, trimethylsilyl, $C_3$–$C_8$-alkyl, $C_1$–$C_4$-alkoxycarbonyl, phenyl-$C_1$–$C_6$-alkyl or phenyl-$C_3$–$C_6$-alkenyl, wherein each aromatic moiety may furthermore carry 1–5 halogen atoms or up to 3 of the following substituents: $C_1$–$C_6$-alkyl, partially or completely halogenated $C_1$–$C_6$-alkyl or $C_1$–$C_6$-alkoxy, with the proviso that when $R^1$ is trifluoromethyl or trimethylsilyl, X is =CH—.

2. The ortho-substituted benzyl ester of a cyclopropanecarboxylic acid of the formula I as claimed in claim 1, wherein X is =N— or =CH—, and $R^1$ is cyano, trifluoromethyl, trimethylsilyl, $C_3$–$C_4$-alkyl, $C_1$–$C_2$-alkoxycarbonyl, phenyl-$C_1$–$C_4$-alkyl or phenyl-$C_3$–$C_4$-alkenyl, wherein each aromatic moiety may furthermore be monosubstituted by halogen or methyl, with the proviso that X is =CH— when $R^1$ is trifluoromethyl or trimethylsilyl.

3. The ortho-substituted benzyl ester of a cyclopropanecarboxylic acid of the formula I as claimed in claim 1, wherein X is =N— and $R^1$ is cyano, $C_3$–$C_8$-alkyl, $C_1$–$C_4$-alkoxycarbonyl, phenyl-$C_1$–$C_6$-alkyl or phenyl-$C_3$–$C_6$-alkenyl, wherein each aromatic moiety may furthermore carry 1–5 halogen atoms or up to 3 of the following substituents: $C_1$–$C_6$-alkyl, partially or completely halogenated $C_1$–$C_6$-alkyl or $C_1$–$C_6$-alkoxy.

4. The ortho-substituted benzyl ester of a cyclopropanecarboxylic acid of the formula I as claimed in claim 1, wherein X is =CH—, and $R^1$ is cyano, trifluoromethyl, trimethylsilyl, $C_3$–$C_8$-alkyl, $C_1$–$C_4$-alkoxycarbonyl, phenyl-$C_1$–$C_6$-alkyl or phenyl-$C_3$–$C_6$-alkenyl, wherein each aromatic moiety may furthermore carry 1–5 halogen atoms or up to 3 of the following substituents: $C_1$–$C_6$-alkyl, partially or completely halogenated $C_1$–$C_6$-alkyl or $C_1$–$C_6$-alkoxy.

5. The ortho-substituted benzyl ester of a cyclopropanecarboxylic acid of claim 1, wherein $R^1$ is n-propyl and X is CH.

6. The ortho-substituted benzyl ester of a cyclopropanecarboxylic acid of claim 1, wherein $R^1$ is n-propyl and X is N.

7. The ortho-substituted benzyl ester of a cyclopropanecarboxylic acid of claim 1, wherein $R^1$ is alkyl and X is CH.

8. A fungicidal composition, comprising: a solid or liquid carrier and a fungicidally effective amount of an ortho-substituted benzyl ester of a cyclopropanecarboxylic acid of formula I as claimed in claim 1.

9. A pesticidal composition, comprising: an inert carrier and a pesticidally effective amount of an ortho-substituted benzyl ester of a cyclopropanecarboxylic acid of formula I as claimed in claim 1.

* * * * *